(12) United States Patent
Nishimura et al.

(10) Patent No.: US 7,087,579 B2
(45) Date of Patent: Aug. 8, 2006

(54) GLUCOPYRANOSYLOXYPYRAZOLE DERIVATIVES AND MEDICINAL USE THEREOF

(75) Inventors: Toshihiro Nishimura, Nagano (JP); Nobuhiko Fushimi, Nagano (JP); Hideki Fujikura, Nagano (JP); Kenji Katsuno, Nagano (JP); Yoshimitsu Komatsu, Nagano (JP); Masayuki Isaji, Nagano (JP)

(73) Assignee: Kissei Pharmaceutical Co., Ltd., Nagano (JP)

( * ) Notice: Subject to any disclaimer, the term of this patent is extended or adjusted under 35 U.S.C. 154(b) by 0 days.

(21) Appl. No.: 10/468,454

(22) PCT Filed: Feb. 26, 2002

(86) PCT No.: PCT/JP02/01707

§ 371 (c)(1),
(2), (4) Date: Feb. 19, 2004

(87) PCT Pub. No.: WO02/068439

PCT Pub. Date: Sep. 6, 2002

(65) Prior Publication Data

US 2004/0132669 A1    Jul. 8, 2004

(30) Foreign Application Priority Data

Feb. 26, 2001  (JP)  ............................. 2001-051278
Feb. 27, 2001  (JP)  ............................. 2001-052903

(51) Int. Cl.
*A01N 43/04* (2006.01)
*A61K 31/70* (2006.01)
*C07H 17/00* (2006.01)

(52) U.S. Cl. .................... 514/27; 514/25; 514/35; 536/4.1; 536/17.4; 536/18.1

(58) Field of Classification Search ............... 536/4.1, 536/17.4, 18.1; 514/25, 35, 27
See application file for complete search history.

(56) References Cited

U.S. PATENT DOCUMENTS

| 5,264,451 | A | 11/1993 | Kees |
| 5,274,111 | A | 12/1993 | Kees |
| 5,424,406 | A | 6/1995 | Tsujihara et al. |
| 5,731,292 | A | 3/1998 | Tsujihara et al. |
| 6,815,428 | B1* | 11/2004 | Ohsumi et al. ............ 514/25 |
| 6,908,905 | B1 | 6/2005 | Ohsumi et al. |
| 2003/0087843 | A1* | 5/2003 | Washburn ................. 514/43 |
| 2004/0116357 | A1 | 1/2004 | Fushimi et al. |
| 2004/0063646 | A1 | 4/2004 | Fujikura et al. |
| 2004/0110936 | A1* | 6/2004 | Ohsumi et al. ............ 536/17.4 |
| 2004/0147729 | A1* | 7/2004 | Fujikura et al. ............ 536/17.4 |

FOREIGN PATENT DOCUMENTS

| CA | 2038428 A1 | 9/1991 |
| EP | 449699 A2 | 10/1991 |
| EP | 1 213 296 A1 * | 3/2001 |
| WO | WO 0116147 A1 | 3/2001 |
| WO | WO 02/36602 A1 | 5/2002 |
| WO | WO 02053573 A1 | 7/2002 |
| WO | WO 02068440 A1 | 9/2002 |
| WO | WO 02/088157 A1 | 11/2002 |

OTHER PUBLICATIONS

Kenneth L. Kees, et al.; New Potent Antihyperglycemic Agents in db/db Mice: synthesis and Structuc-Activity Relationship Studies of (4-Substitutedbenzyl) (Trifluoromethyl) pyrazoles and-pyrazolones, J. Med. Chem., 1990, vol. 39, No. 20, pp. 3920-3928.

* cited by examiner

*Primary Examiner*—James O. Wilson
*Assistant Examiner*—Traviss C. McIntosh, III
(74) *Attorney, Agent, or Firm*—Sughrue Mion, PLLC

(57) ABSTRACT

The present invention provides glucopyranosyloxypyrazole derivatives represented by the general formula:

(I)

wherein one of Q and T represents a group represented by the general formula:

while the other represents a lower alkyl group or a halo (lower alkyl) group; $R^1$ represents a hydrogen atom, an optionally substituted lower alkyl group, a lower alkenyl group, a cyclic lower alkyl group, etc.; $R^2$ represents a hydrogen atom, an optionally substituted lower alkyl group, a lower alkoxy group, a lower alkenyl group, a cyclic lower alkyl group, a cyclic lower alkoxy group, etc., which exert an excellent inhibitory activity in human SGLT2, and therefore are useful as drugs for the prevention or treatment of a disease associated with hyperglycemia such as diabetes, diabetic complications or obesity, pharmaceutically acceptable salts thereof or prodrugs thereof, production intermediates thereof and pharmaceutical uses thereof.

4 Claims, No Drawings

GLUCOPYRANOSYLOXYPYRAZOLE DERIVATIVES AND MEDICINAL USE THEREOF

This is a 371 of PCT/JP02/01707, and claims benefit from Japanese Applications 51278/2001 filed Feb. 26, 2001 and 52903/2001 filed Feb. 27, 2001, each of which is incorporated herein by reference.

TECHNICAL FIELD

The present invention relates to glucopyranosyloxypyrazole derivatives, pharmaceutically acceptable salts thereof or prodrugs thereof which are useful as medicaments, production intermediates thereof and pharmaceutical uses thereof.

More particularly, the present invention relates to glucopyranosyloxypyrazole derivatives which have an inhibitory activity in human SGLT2, represented by the general formula:

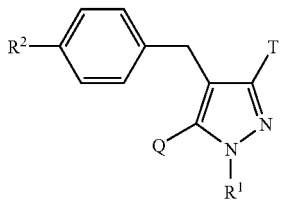

(I)

wherein one of Q and T represents a group represented by the general formula:

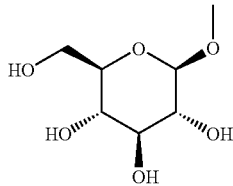

while the other represents a lower alkyl group or a halo (lower alkyl) group; $R^1$ represents a hydrogen atom, a lower alkyl group, a lower alkenyl group, a cyclic lower alkyl group, a cyclic lower alkyl-substituted (lower alkyl) group or a group represented by the general formula: HO-$A^1$- wherein $A^1$ represents a lower alkylene group; $R^2$ represents a hydrogen atom, a lower alkyl group, a lower alkoxy group, a lower alkylthio group, a halo(lower alkyl) group, a halogen atom, a lower alkenyl group, a cyclic lower alkyl group, a cyclic lower alkoxy group, a cyclic lower alkylidenemethyl group, a phenyl group which may have 1–3 different or same groups selected from a halogen atom and a hydroxy group, a 5- or 6-membered aromatic heterocyclic group which contains 1–4 different or same atoms selected from an oxygen atom, a sulfur atom and a nitrogen atom in the ring, or a group represented by the general formula: HO-$A^2$- wherein $A^2$ represents a lower alkylene group; and with the proviso that $R^2$ does not represent either a hydrogen atom, a lower alkyl group, a lower alkoxy group, a lower alkylthio group, a halo(lower alkyl) group or a halogen atom when $R^1$ represents a hydrogen atom or a lower alkyl group, or pharmaceutically acceptable salts thereof and prodrugs thereof which are useful as agents for the prevention or treatment of a disease such as diabetes, diabetic complications or obesity.

BACKGROUND ART

Diabetes is one of lifestyle-related diseases with the background of change of eating habit and lack of exercise. Hence, diet and exercise therapies are performed in patients with diabetes. Furthermore, when its sufficient control and continuous performance are difficult, drug treatment is simultaneously performed. Now, biguanides, sulfonylureas and insulin sensitivity enhancers have been employed as antidiabetic agents. However, biguanides and sulfonylureas show occasionally adverse effects such as lactic acidosis and hypoglycemia, respectively. In a case of using insulin sensitivity enhancers, adverse effects such as edema are occasionally observed, and it is also concerned for advancing obesity. Therefore, in order to solve these problems, it has been desired to develop antidiabetic agents having a new mechanism.

In recent years, development of new type antidiabetic agents has been progressing, which promote urinary glucose excretion and lower blood glucose level by preventing excess glucose reabsorption at the kidney (J. Clin. Invest., Vol. 79, pp. 1510–1515 (1987)). In addition, it is reported that SGLT2 ($Na^+$/glucose cotransporter 2) is present in the S1 segment of the kidney's proximal tubule and participates mainly in reabsorption of glucose filtrated through glomerular (J. Clin. Invest., Vol. 93, pp. 397–404 (1994)). Accordingly, inhibiting a human SGLT2 activity prevents reabsorption of excess glucose at the kidney, subsequently promotes excreting excess glucose though the urine, and normalizes blood glucose level. Therefore, fast development of antidiabetic agents, which have a potent inhibitory activity in human SGLT2 and have a new mechanism, has been desired. In addition, since such agents promote the excretion of excess glucose though the urine and consequently the glucose accumulation in the body is decreased, they are also expected to have a preventing or alleviating effect on obesity and a urinating effect. Furthermore, the agents are considered to be useful for various related diseases which occur accompanying the progress of diabetes or obesity due to hyperglycemia.

As compounds having pyrazole moiety, it is described that WAY-123783 increased an amount of excreted glucose in normal mice. However, its effects in human are not described at all (J. Med. Chem., Vol. 39, pp. 3920–3928 (1996)).

DISCLOSURE OF THE INVENTION

The present inventors have studied earnestly to find compounds having an inhibitory activity in human SGLT2. As a result, it was found that compounds represented by the above general formula (I) show an excellent inhibitory activity in human SGLT2, thereby forming the basis of the present invention.

The present invention is to provide the following glucopyranosyloxypyrazole derivatives, pharmaceutically acceptable salts thereof and prodrugs thereof which exert an inhibitory activity in human SGLT2 and show an excellent hypoglycemic effect by excreting excess glucose in the urine through preventing the reabsorption of glucose at the kidney, and production intermediates thereof, and to provide pharmaceutical uses thereof.

This is, the present invention relates to a glucopyranosyloxypyrazole derivative represented by the general formula:

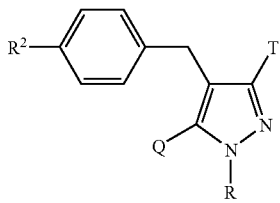

wherein one of Q and T represents a group represented by the general formula:

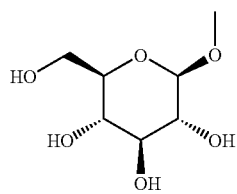

while the other represents a lower alkyl group or a halo (lower alkyl) group; $R^1$ represents a hydrogen atom, a lower alkyl group, a lower alkenyl group, a cyclic lower alkyl group, a cyclic lower alkyl-substituted (lower alkyl) group or a group represented by the general formula: HO-$A^1$- wherein $A^1$ represents a lower alkylene group; $R^2$ represents a hydrogen atom, a lower alkyl group, a lower alkoxy group, a lower alkylthio group, a halo(lower alkyl) group, a halogen atom, a lower alkenyl group, a cyclic lower alkyl group, a cyclic lower alkoxy group, a cyclic lower alkylidenemethyl group, a phenyl group which may have 1–3 different or same groups selected from a halogen atom and a hydroxy group, a 5- or 6-membered aromatic heterocyclic group which contains 1–4 different or same atoms selected from an oxygen atom, a sulfur atom and a nitrogen atom in the ring, or a group represented by the general formula: HO-$A^2$- wherein $A^2$ represents a lower alkylene group; and with the proviso that $R^2$ does not represent either a hydrogen atom, a lower alkyl group, a lower alkoxy group, a lower alkylthio group, a halo(lower alkyl) group or a halogen atom when $R^1$ represents a hydrogen atom or a lower alkyl group, pharmaceutically acceptable salts thereof or prodrugs thereof.

Also, the present invention relates to a pharmaceutical composition, a human SGLT2 inhibitor and an agent for the prevention or treatment of a disease associated with hyperglycemia, which comprise as an active ingredient a glucopyranosyloxypyrazole derivative represented by the above general formula (I), a pharmaceutically acceptable salt thereof or a prodrug thereof.

The present invention relates to a method for the prevention or treatment of a disease associated with hyperglycemia, which comprises administering an effective amount of a glucopyranosyloxypyrazole derivative represented by the above general formula (I), a pharmaceutically acceptable salt thereof or a prodrug thereof.

The present invention relates to a use of a glucopyranosyloxypyrazole derivative represented by the above general formula (I), a pharmaceutically acceptable salt thereof or a prodrug thereof for the manufacture of a pharmaceutical composition for the prevention or treatment of a disease associated with hyperglycemia.

The present invention relates to a pharmaceutical combination which comprises (A) a glucopyranosyloxypyrazole derivative represented by the above general formula (I), a pharmaceutically acceptable salt thereof or a prodrug thereof, and (B) at least one member selected from the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhidantoin, EGB-761, bimoclomol, sulodexide, Y-128, a hydroxymethyl-glutaryl coenzyme A reductase inhibitor, a fibric acid derivative, a $β_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $α_2$-adrenoceptor agonist, an antiplatelets agent, a uric acid synthesis inhibitor, a uricosuric agent and a urinary alkalinizer.

The present invention relates to a method for the prevention or treatment of a disease associated with hyperglycemia, which comprises administering an effective amount of (A) a glucopyranosyloxypyrazole derivative represented by the above general formula (I), a pharmaceutically acceptable salt thereof or a prodrug thereof, in combination with (B) at least one member selected from the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhidantoin, EGB-761, bimoclomol, sulodexide, Y-128, a hydroxymethyl-glutaryl coenzyme A reductase inhibitor, a fibric acid derivative, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer.

The present invention relates to a use of (A) a glucopyranosyloxypyrazole derivative represented by the above general formula (I), a pharmaceutically acceptable salt thereof or a prodrug thereof, and (B) at least one member selected from the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhidantoin, EGB-761, bimoclomol, sulodexide, Y-128, a hydroxymethylglutaryl coenzyme A reductase inhibitor, a fibric acid derivative, a $\beta_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $\alpha_2$-adrenoceptor agonist, an antiplatelets agent, a uric acid synthesis inhibitor, a uricosuric agent and a urinary alkalinizer, for the manufacture of a pharmaceutical composition for the prevention or treatment of a disease associated with hyperglycemia.

Furthermore, the present invention relates to a glucopyranosyloxypyrazole derivative represented by the general formula:

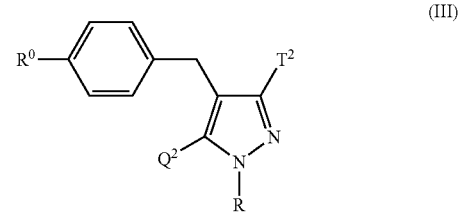

(III)

wherein one of $Q^2$ and $T^2$ represents 2,3,4,6-tetra-O-acetyl-β-D-glucopyranosyloxy group and the other represents a lower alkyl group or a halo(lower alkyl) group; R represents a hydrogen atom, a lower alkyl group, a lower alkenyl group, a cyclic lower alkyl group, a cyclic lower alkyl-substituted (lower alkyl) group or a group represented by the general formula: $P^{10}$-$A^1$- wherein $P^{10}$ represents a hydrogen atom or a hydroxy-protective group; and $A^1$ represents a lower alkylene group; $R^0$ represents a hydrogen atom, a lower alkyl group, a lower alkoxy group, a lower alkylthio group, a halo(lower alkyl) group, a halogen atom, a lower alkenyl group, a cyclic lower alkyl group, a cyclic lower alkoxy group, a cyclic lower alkylidenemethyl group, a phenyl group which may have 1–3 different or same groups selected from a halogen atom and a hydroxy group, a 5- or 6-membered aromatic heterocyclic group which contains 1–4 different or same atoms selected from an oxygen atom, a sulfur atom and a nitrogen atom in the ring, or a group represented by the general formula: $P^{20}$-O-$A^2$- wherein $P^{20}$ represents a hydrogen atom or a hydroxy-protective group; and $A^2$ represents a lower alkylene group; and with the proviso that $R^0$ does not represent either a hydrogen atom, a lower alkyl group, a lower alkoxy group, a lower alkylthio group, a halo(lower alkyl) group or a halogen atom when R represents a hydrogen atom or a lower alkyl group, or a pharmaceutically acceptable salt thereof, and a glucopyranosyloxypyrazole derivative represented by the general formula:

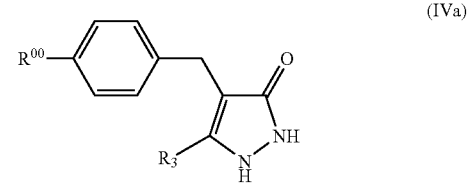

(IVa)

wherein $R^{00}$ represents a lower alkenyl group, a cyclic lower alkyl group, a cyclic lower alkoxy group, a cyclic lower alkylidenemethyl group, a phenyl group which may have 1–3 different or same groups selected from a halogen atom and a hydroxy group, a 5- or 6-membered aromatic heterocyclic group which contains 1–4 different or same atoms selected from an oxygen atom, a sulfur atom and a nitrogen atom in the ring, or a group represented by the general formula: $P^{20}$-$A^2$- wherein $P^{20}$ represents a hydrogen atom or a hydroxy-protective group; and $A^2$ represents a lower alkylene group; $R^3$ represents a lower alkyl group or a halo(lower alkyl) group, or a pharmaceutically acceptable salt thereof.

As prodrugs of the above mentioned glucopyranosyloxy-pyrazole derivatives, a compound represented by the general formula:

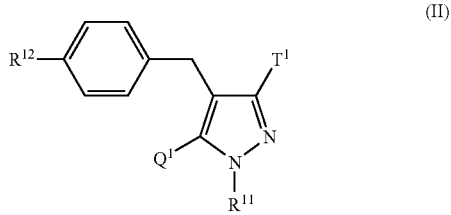

(II)

wherein one of $Q^1$ and $T^1$ represents a group represented by the general formula:

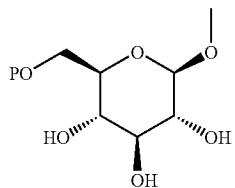

wherein P represents a hydrogen atom or a group forming prodrug; and the other represents a lower alkyl group or a halo(lower alkyl) group; $R^{11}$ represents a hydrogen atom, a lower alkyl group, a lower alkenyl group, a cyclic lower alkyl group, a cyclic lower alkyl-substituted (lower alkyl) group, a group forming prodrug or a group represented by the general formula: $P^1$-$A^1$- wherein $P^1$ represents a hydrogen atom or a group forming prodrug; and $A^1$ represents a lower alkylene group; $R^{12}$ represents a hydrogen atom, a lower alkyl group, a lower alkoxy group, a lower alkylthio group, a halo(lower alkyl) group, a halogen atom, a lower alkenyl group, a cyclic lower alkyl group, a cyclic lower alkoxy group, a cyclic lower alkylidenemethyl group, a phenyl group which may have 1–3 different or same groups selected from a halogen atom and a hydroxy group, a 5- or 6-membered aromatic heterocyclic group which contains 1–4 different or same atoms selected from an oxygen atom, a sulfur atom and a nitrogen atom in the ring, or a group represented by the general formula: $P^2$-$A^2$- wherein $P^2$ represents a hydrogen atom or a group forming prodrug; and $A^2$ represents a lower alkylene group; and with the proviso that $R^{12}$ does not represent either a hydrogen atom, a lower alkyl group, a lower alkoxy group, a lower alkylthio group, a halo(lower alkyl) group or a halogen atom when at least one of P, $R^{11}$ and $R^{12}$ represents a group forming prodrug and $R^{11}$ represents a hydrogen atom or a lower alkyl group are illustrated.

In the present invention, the term "prodrug" means a compound which is converted into a glucopyranosyloxy-pyrazole derivative represented by the above general formula (I) as an active form thereof in vivo. As examples of groups forming prodrugs, in cases of such groups located at a hydroxy group, a hydroxy-protective group used generally as a prodrug such as a lower acyl group, a lower alkoxy-substituted (lower acyl) group, a lower alkoxycarbonyl-substituted (lower acyl) group, a lower alkoxycarbonyl group and a lower alkoxy-substituted (lower alkoxycarbonyl) group are illustrated, and in cases of such groups located at a nitrogen atom, an amino-protective group used generally as a prodrug such as a lower acyl group, a lower alkoxycarbonyl group, a lower acyloxymethyl group and a lower alkoxycarbonyloxymethyl group are illustrated.

In the present invention, the term "lower alkyl group" means a straight-chained or branched alkyl group having 1 to 6 carbon atoms such as a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a hexyl group or the like; the term "lower alkoxy group" means a straight-chained or branched alkoxy group having 1 to 6 carbon atoms such as a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a tert-pentyloxy group, a hexyloxy group or the like; and the term "lower alkylthio group" means a straight-chained or branched alkylthio group having 1 to 6 carbon atoms such as a methylthio group, an ethylthio group, a propylthio group, an isopropylthio group, a butylthio group, an isobutylthio group, a sec-butylthio group, a tert-butylthio group, a pentylthio group, an isopentylthio group, a neopentylthio group, a tert-pentylthio group, a hexylthio group or the like. The term "lower alkylene group" means a straight-chained or branched alkylene group having 1 to 6 carbon atoms such as a methylene group, an ethylene group, a trimethylene group, a propylene group or the like; the term "lower alkenyl group" means a straight-chained or branched alkenyl group having 2 to 6 carbon atoms such as a vinyl group, an allyl group, a 1-propenyl group, an isopropenyl group, a 1-butenyl group, a 2-butenyl group, a 2-methylallyl group, a 2-methyl-1-propenyl group or the like; the term "cyclic lower alkyl group" means a 3- to 7-member cyclic alkyl group such as a cyclopropyl group, a cyclobutyl group, a cyclopentyl group, a cyclohexyl group, a cycloheptyl group or the like; the term "cyclic lower alkoxy group" means a 3- to 7-membered cyclic alkoxy group such as a cyclopropyloxy group, a cyclobutyloxy group, a cyclopentyloxy group, a cyclohexyloxy group, a cycloheptyloxy group or the like; and the term "cyclic lower alkylidenemethyl group" means a 3- to 6-membered cyclic alkylidenemethyl group such as a cyclopropylidenemethyl group, a cyclobutylidenemethyl group, a cyclopentylidenemethyl group, a cyclohexylidenemethyl group or the like. The term "halogen atom" means a fluorine atom, a chlorine atom, a bromine atom or an iodine atom; and the term "halo(lower alkyl) group" means the above lower alkyl group substituted by 1 to 3 different or same halogen atoms defined above. The term "lower acyl group" means a straight-chained, branched or cyclic acyl group having 2 to 7 carbon atoms such as an acetyl group, a propionyl group, a butyryl group, an isobutyryl group, a pivaloyl group, a hexanoyl group, a cyclohexylcarbonyl group or the like; and the term "lower alkoxy-substituted (lower acyl) group means the above lower acyl group substituted by the above lower alkoxy group. The term "lower alkoxycarbonyl group" means a straight-chained, branched or cyclic alkoxy-carbonyl group having 2 to 7 carbon atoms such as a methoxycarbonyl group, an ethoxycarbonyl group, a propyloxycarbonyl group, an isopropyloxycarbonyl group, a butyloxycarbonyl group, an isobutyloxycarbonyl group, a sec-butyloxycarbonyl group, a tert-butyloxycarbonyl group, a pentyloxycarbonyl group, an isopentyloxycarbonyl group, a neo-pentyloxycarbonyl group, a tert-pentyloxycarbonyl group, a hexyloxycarbonyl group, and a cyclohexyloxycar-bonyl group; the term "lower alkoxycarbonyl-substituted (lower acyl) group means the above lower acyl group substituted by the above lower alkoxycarbonyl group such as a 3-(ethoxycarbonyl)propionyl group; and the term "lower alkoxy-substituted (lower alkoxycarbonyl) group means the above lower alkoxycarbonyl group substituted by the above alkoxy group such as a 2-methoxyethoxycarbonyl group. The term "lower acyloxymethyl group" means a hydroxymethyl group O-substituted by the above lower acyl group; and the term "lower alkoxycarbonyloxymethyl group" means a hydroxymethyl group O-substituted by the above lower alkoxycarbonyl group. The term "5- or 6-membered aromatic heterocyclic group which contains 1–4 different or same atoms selected from an oxygen atom, a sulfur atom and a nitrogen atom in the ring" means a univalent group derived from an aromatic heterocycle such as furan, thiophene, pyrrole, oxazole, isoxazole, thiazole, isothiazole, pyrazole, imidazole, furazan, tetrazole, pyridine, pyridazine, pyrimidine, pyrazine, triazine or the like. The term "hydroxy-protective group" means a hydroxy-protective group used in general organic synthesis such as a benzyl group, a methoxymethyl group, an acetyl group or the like.

The glucopyranosyloxypyrazole derivatives represented by the above general formula (I) of the present invention and prodrugs thereof can be prepared according to the following procedure:

wherein X and Y represent a leaving group such as a halogen atom, a mesyloxy group or a tosyloxy group; $R^3$ represents a lower alkyl group or a halo(lower alkyl) group; $R^4$ represents a methyl group or an ethyl group; $R^5$ represents a lower alkyl group, a lower alkenyl group, a cyclic lower alkyl group, a cyclic lower alkyl-substituted (lower alkyl) group or a group represented by the general formula: $P^{10}$-$A^1$- wherein $P^{10}$ and $A^1$ have the same meanings as defined above; and R, $R^0$, $R^1$, $R^2$, Q, $Q^2$, T and $T^2$ have the same meanings as defined above.

Process 1

A compound represented by the above general formula (VII) can be prepared by condensing a benzyl derivative represented by the above general formula (V) with a ketoacetate represented by the above general formula (VI) in the presence of a base such as sodium hydride or potassium tert-butoxide in an inert solvent. As the inert solvent used in the reaction, 1,2-dimethoxyethane, tetrahydrofuran, N,N-dimethylformamide, a mixed solvent thereof and the like

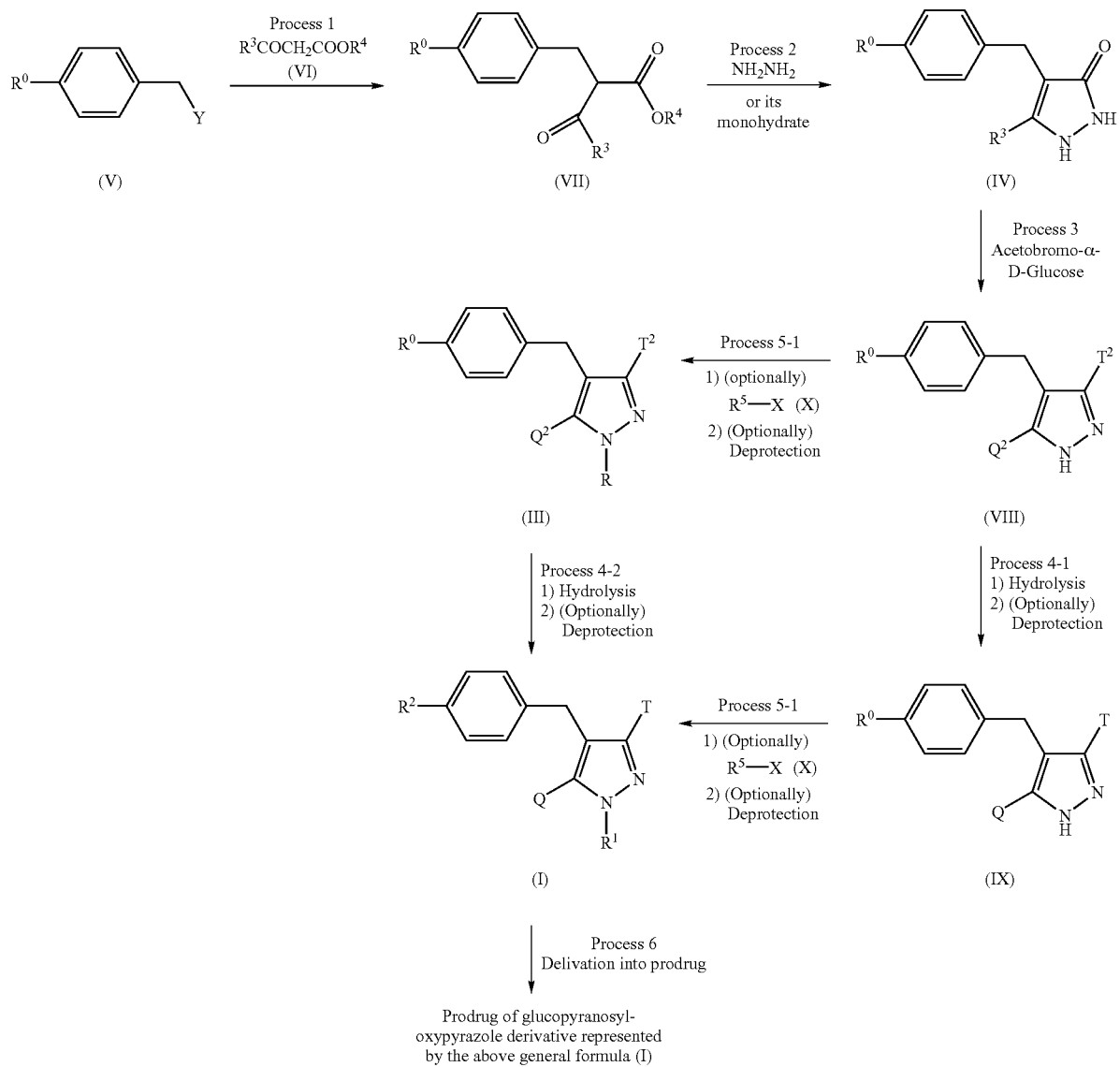

can be illustrated. The reaction temperature is usually from room temperature to reflux temperature, and the reaction time is usually from 1 hour to 1 day, varying based on a used starting material, solvent and reaction temperature.

Process 2

A benzylpyrazole derivative represented by the above general formula (IV) of the present invention can be prepared by condensing a compound represented by the above general formula (VII) with hydrazine or hydrazine monohydrate in an inert solvent. As the inert solvent used in the reaction, toluene, tetrahydrofuran, chloroform, a mixed solvent thereof and the like can be illustrated. The reaction temperature is usually from room temperature to reflux temperature, and the reaction time is usually from 1 hour to 1 day, varying based on a used starting material, solvent and reaction temperature. The obtained pyrazolone derivative represented by the above general formula (IV) can be also used in process 3 after converting into a salt thereof in a usual way.

Process 3

1) In case of benzylpyrazole derivatives represented by the above general formula (IV) wherein $R^3$ is a lower alkyl group, a corresponding compound represented by the above general formula (VIII) can be prepared by subjecting a corresponding benzylpyrazole derivative represented by the above general formula (IV) to glycosidation using acetobromo-α-D-glucose in the presence of a base such as silver carbonate in an inert solvent. As the solvent used in the glycosidation reaction, tetrahydrofuran and the like can be illustrated. The reaction temperature is usually from room temperature to reflux temperature, and the reaction time is usually from 1 hour to 1 day, varying based on a used starting material, solvent and reaction temperature.

2) In case of benzylpyrazole derivatives represented by the above general formula (IV) wherein $R^3$ is a halo(lower alkyl) group, a corresponding compound represented by the above general formula (VIII) can be prepared by subjecting a corresponding benzylpyrazole derivative represented by the above general formula (IV) to glycosidation using acetobromo-α-D-glucose in the presence of a base such as potassium carbonate in an inert solvent. As the solvent used in the glycosidation reaction, acetonitrile, tetrahydrofuran and the like can be illustrated. The reaction temperature is usually from room temperature to reflux temperature, and the reaction time is usually from 1 hour to 1 day, varying based on a used starting material, solvent and reaction temperature.

In the compounds represented by the above general formula (IV) of the present invention as starting materials, there can be the following three tautomers, varying based on the change of reaction conditions. The compounds represented by the above general formula (IV) of the present invention include all compounds described as the following states:

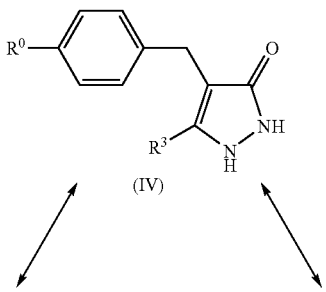

-continued

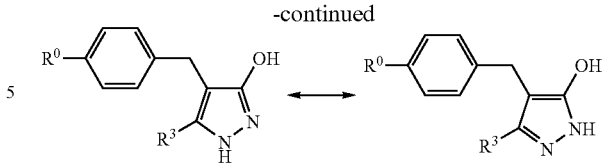

wherein $R^0$ and $R^3$ have the same meanings as defined above.

Process 4-1

A glucopyranosyloxypyrazole derivative represented by the above general formula (IX) can be prepared by subjecting a compound represented by the above general formula (VIII) to alkaline hydrolysis and optionally removal of a hydroxy-protective group in a usual way. As the solvent used in the alkaline hydrolysis, methanol, ethanol, tetrahydrofuran, water, a mixed solvent thereof and the like can be illustrated, and as the base used, sodium hydroxide, sodium methoxide, sodium ethoxide and the like can be illustrated. The reaction temperature is usually from 0° C. to room temperature, and the reaction time is usually from 30 minutes to 6 hours, varying based on a used starting material, solvent and reaction temperature.

Process 4-2

A glucopyranosyloxypyrazole derivative represented by the above general formula (I) of the present invention can be prepared by subjecting a compound represented by the above general formula (III) to alkaline hydrolysis and optionally removal of a hydroxy-protective group in a usual way. As the solvent used in the hydrolysis reaction, methanol, ethanol, tetrahydrofuran, water, a mixed solvent thereof and the like can be illustrated, and as the base, sodium hydroxide, sodium methoxide, sodium ethoxide and the like can be illustrated. The reaction temperature is usually from 0° C. to room temperature, and the reaction time is usually from 30 minutes to 6 hours, varying based on a used starting material, solvent and reaction temperature.

Process 5-1

A compound represented by the above general formula (III) of the present invention can be prepared by subjecting a glucopyranosyloxypyrazole derivative represented by the above general formula (VIII) to N-alkylation optionally using an N-alkylating agent represented by the above general formula (X) in the presence of a base such as potassium carbonate or cesium carbonate in an inert solvent, and optionally to deprotection in a usual way. As the inert solvent used in the N-alkylation, acetonitrile, N,N-dimethylformamide, tetrahydrofuran, a mixed solvent thereof and the like can be illustrated. The reaction temperature is usually from room temperature to reflux temperature, and the reaction time is usually from 30 minutes to 1 day, varying based on a used starting material, solvent and reaction temperature. The obtained compound represented by the above general formula (III) can be also used in process 4-2 after converting into a salt thereof in a usual way.

Process 5-2

A compound represented by the above general formula (I) of the present invention can be prepared by subjecting a glucopyranosyloxypyrazole derivative represented by the above general formula (IX) to N-alkylation optionally using an N-alkylating agent represented by the above general formula (X) in the presence of a base such as potassium carbonate or cesium carbonate, and occasionally a catalytic amount of sodium iodide in an inert solvent, and optionally to deprotection in a usual way. As the inert solvent used in the N-alkylation, N,N-dimethylformamide, 1,2-dimethoxyethane, dimethyl sulfoxide, tetrahydrofuran, ethanol, a mixed solvent thereof and the like can be illustrated. The reaction temperature is usually from room temperature to reflux temperature, and the reaction time is usually from 10 minutes to 1 day, varying based on a used starting material, solvent and reaction temperature.

Process 6

A prodrug of a glucopyranosyloxypyrazole derivative represented by the above general formula (I) (including a prodrug represented by the above general formula (II)) can be prepared by introducing hydroxy- and/or amino-protective groups generally capable for use in a prodrug into a hydroxy group and/or a nitrogen atom of a glucopyranosyloxypyrazole derivative represented by the above general formula (II) in a usual way.

For example, the derivation reaction to a prodrug in the above process 6 can be done according to the following procedure or analogous procedures thereof:

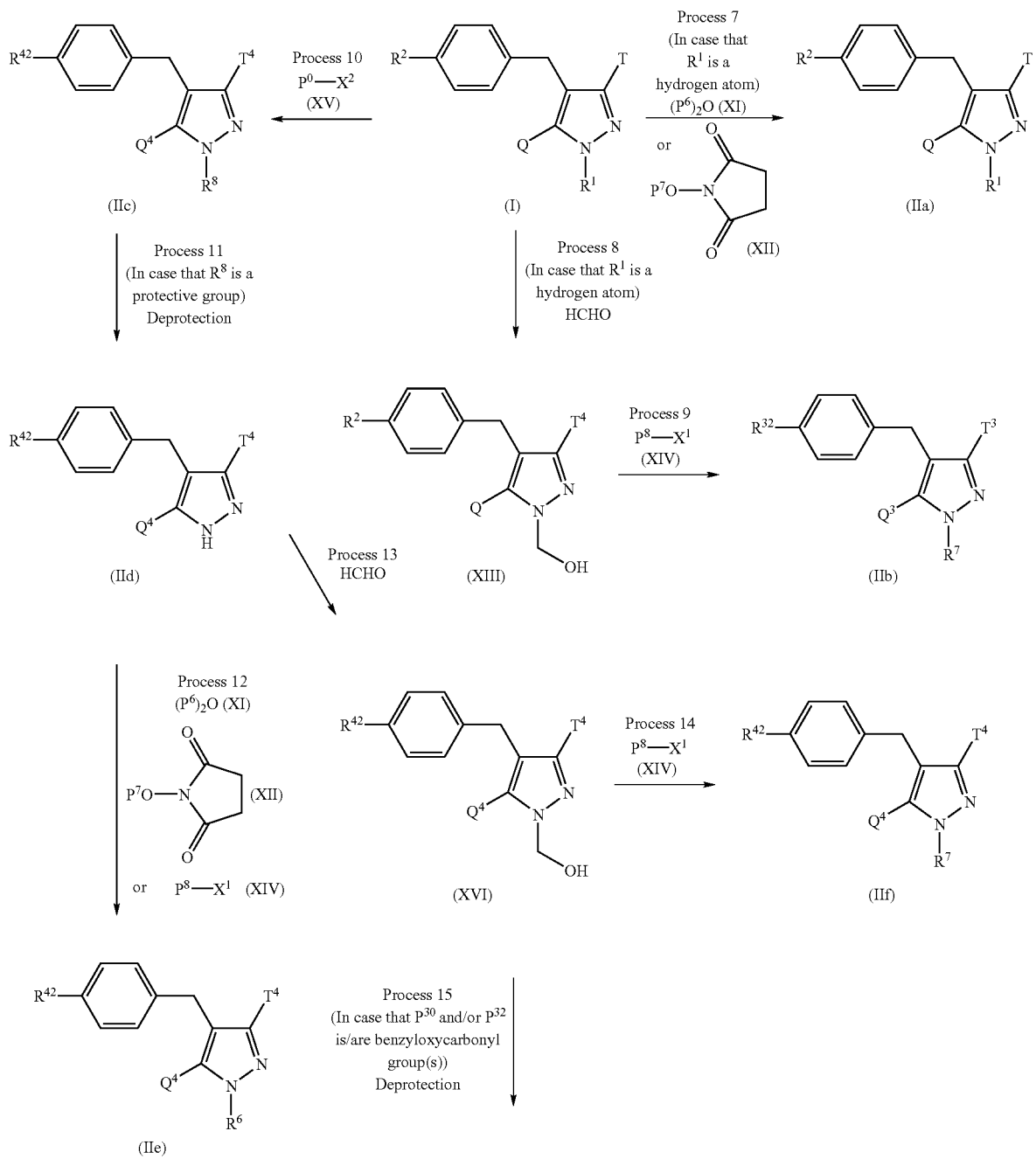

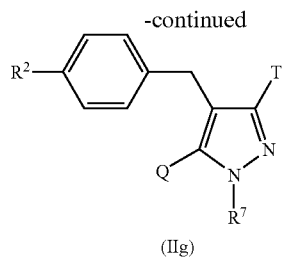

(IIg)

wherein $P^0$ represents a hydroxy-protective group such as a lower acyl group, a lower alkoxy-substituted (lower acyl) group, a lower alkoxycarbonyl-substituted (lower acyl) group, a lower alkoxycarbonyl group, a lower alkoxy-substituted (lower alkoxycarbonyl) group or a benzyloxycarbonyl group; $P^6$ represents a lower acyl group; $P^7$ represents a lower alkoxycarbonyl group; $P^8$ represents a lower acyl group or a lower alkoxycarbonyl group; $R^6$ represents a lower acyl group or a lower alkoxycarbonyl group; $R^7$ represents a lower acyloxymethyl group or a lower alkoxycarbonyloxymethyl group; $R^8$ represents a lower alkyl group, a lower alkenyl group, a cyclic lower alkyl group, a cyclic lower alkyl-substituted (lower alkyl) group, a lower acyl group, a lower alkoxy-substituted (lower acyl) group, a lower alkoxycarbonyl-substituted (lower acyl) group, a lower alkoxycarbonyl group, a lower alkoxy-substituted (lower alkoxycarbonyl) group, a benzyloxycarbonyl group, or a group represented by the general formula: $P^{21}$—O-$A^1$- wherein $P^{21}$ represents a hydrogen atom or a hydroxy-protective group such as a lower acyl group, a lower alkoxy-substituted (lower acyl) group, a lower alkoxycarbonyl-substituted (lower acyl) group, a lower alkoxycarbonyl group, a lower alkoxy-substituted (lower alkoxycarbonyl) group or a benzyloxycarbonyl group; and $A^1$ represents a lower alkylene group; $X^1$ and $X^2$ represent a leaving group such as a bromine atom or a chlorine atom; one of $Q^3$ and $T^3$ represents a group represented by the general formula:

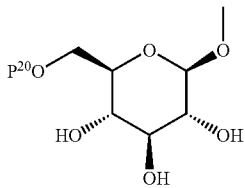

wherein $P^{20}$ represents a hydrogen atom, a lower acyl group or a lower alkoxycarbonyl group; and the other represents a lower alkyl group or a halo(lower alkyl) group; $R^{32}$ represents a hydrogen atom, a lower alkyl group, a lower alkoxy group, a lower alkylthio group, a halo(lower alkyl) group, a halogen atom, a lower alkenyl group, a cyclic lower alkyl group, a cyclic lower alkoxy group, a cyclic lower alkylidenemethyl group, or a phenyl group which may have 1–3 different or same groups selected from a halogen atom and a hydroxy group, a 5- or 6-membered aromatic heterocyclic group which contains 1–4 different or same atoms selected from an oxygen atom, a sulfur atom and a nitrogen atom in the ring, or a group represented by the general formula: $P^{22}$—O-$A^2$- wherein $P^{22}$ represents a hydrogen atom, a lower acyl group or a lower alkoxycarbonyl group; and $A^2$ represents a lower alkylene group; and with the proviso that at least one of $P^{20}$ and $P^{22}$ represents a lower acyl group or a lower alkoxycarbonyl group and one of $Q^4$ and $T^4$ represents a group represented by the general formula:

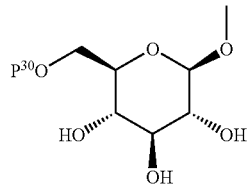

wherein $P^{30}$ represents a hydrogen atom or a hydroxy-protective group such as a lower acyl group, a lower alkoxy-substituted (lower acyl) group, a lower alkoxycarbonyl-substituted (lower acyl) group, a lower alkoxycarbonyl group, a lower alkoxy-substituted (lower alkoxycarbonyl) group or a benzyloxycarbonyl group; and the other represents a lower alkyl group or a halo(lower alkyl) group; $R^{42}$ represents a hydrogen atom, a lower alkyl group, a lower alkoxy group, a lower alkylthio group, a halo(lower alkyl) group, a halogen atom, a lower alkenyl group, a cyclic lower alkyl group, a cyclic lower alkoxy group, a cyclic lower alkylidenemethyl group, or a phenyl group which may have 1–3 different or same groups selected from a halogen atom and a hydroxy group, a 5- or 6-membered aromatic heterocyclic group which contains 1–4 different or same atoms selected from an oxygen atom, a sulfur atom and a nitrogen atom in the ring, or a group represented by the general formula: $P^{32}$—O-$A^2$- wherein $P^{32}$ represents a hydrogen atom or a hydroxy-protective group such as a lower acyl group, a lower alkoxy-substituted (lower acyl) group, a lower alkoxycarbonyl-substituted (lower acyl) group, a lower alkoxycarbonyl group, a lower alkoxy-substituted (lower alkoxycarbonyl) group or a benzyloxycarbonyl group; and $A^2$ represents a lower alkylene group; and with the proviso that at least one of $P^{21}$, $P^{30}$ and $P^{32}$ represents a hydroxy-protective group such as a lower acyl group, a lower alkoxy-substituted (lower acyl) group, a lower alkoxycarbonyl-substituted (lower acyl) group, a lower alkoxycarbonyl group, a lower alkoxy-substituted (lower alkoxycarbonyl) group or a benzyloxycarbonyl group; and $R^1$, $R^2$, Q and T have the same meanings as defined above.

Process 7

A prodrug represented by the above general formula (IIa) can be prepared by protecting a nitrogen atom of a glucopyranosyloxypyrazole derivative represented by the above general formula (I) with an aliphatic acid anhydride represented by the above general formula (XI) in an aliphatic acid such as acetic acid at usually 0° C. to reflux temperature for usually 30 minutes to 1 day, or alternatively, with a succinimide derivative represented by the above general formula (XII) in an inert solvent such as tetrahydrofuran at usually room temperature to reflux temperature for 1 hour to 1 day. The reaction time can be appropriately varied based on a used starting material, solvent and reaction temperature.

Process 8

A compound represented by the above general formula (XIII) can be prepared by introducing a hydroxymethyl group into a nitrogen atom of a glucopyranosyloxypyrazole derivative represented by the above general formula (I) using formaldehyde in a various solvent. As the solvent used in the reaction, water, methanol, ethanol, tetrahydrofuran, dichloromethane, ethyl acetate, N,N-dimethylformamide, acetonitrile, a mixed solvent thereof and the like can be illustrated. The reaction temperature is usually from 0° C. to reflux temperature, and the reaction time is usually from 30 minutes to 1 day, varying based on a used starting material, solvent and reaction temperature.

Process 9

A prodrug represented by the above general formula (IIb) can be prepared by protecting the hydroxymethyl group of a compound represented by the above general formula (XIII) with a reagent for protection represented by the above general formula (XIV) in the presence of a base such as pyridine, triethylamine, N,N-diisopropylethylamine, picoline, lutidine, collidine, quinuclidine, 1,2,2,6,6-pentamethylpiperidine or 1,4-diazabicyclo[2.2.2]octane in an inert solvent or without any solvent. As the inert solvent used in the reaction, dichloromethane, acetonitrile, ethyl acetate, diisopropyl ether, chloroform, tetrahydrofuran, 1,2-dimethoxyethane, 1,4-dioxane, acetone, tert-butanol, a mixed solvent thereof and the like can be illustrated. The reaction temperature is usually from −40° C. to reflux temperature, and the reaction time is usually from 30 minutes to 2 days, varying based on a used starting material, solvent and reaction temperature.

Process 10

A prodrug represented by the above general formula (IIc) or an analogous compound thereof can be prepared by protecting a nitrogen atom and/or a hydroxy group of a glucopyranosyloxypyrazole derivative represented by the above general formula (I) with a reagent for protection represented by the above general formula (XV) in the presence of a base such as pyridine, triethylamine, N,N-diisopropylethylamine, picoline, lutidine, collidine, quinuclidine, 1,2,2,6,6-pentamethylpiperidine or 1,4-diazabicyclo[2.2.2]octane in an inert solvent or without any solvent. As the inert solvent used in the reaction, dichloromethane, acetonitrile, ethyl acetate, diisopropyl ether, chloroform, tetrahydrofuran, 1,2-dimethoxyethane, 1,4-dioxane, acetone, tert-butanol, a mixed solvent thereof and the like can be illustrated. The reaction temperature is usually from −40° C. to reflux temperature, and the reaction time is usually usually from 30 minutes to 2 days, varying based on a used starting material, solvent and reaction temperature.

Process 11

A prodrug represented by the above general formula (IId) or an analogous compound thereof can be prepared by subjecting a compound represented by the above general formula (IIc) to deacylation in the presence of a weak base such as sodium hydrogen carbonate, sodium carbonate or potassium carbonate in an alcoholic solvent such as methanol or ethanol. The reaction temperature is usually from 0° C. to reflux temperature, and the reaction time is usually from 15 minutes to 1 day, varying based on a used starting material, solvent and reaction temperature.

Process 12

A prodrug represented by the above general formula (IIe) or an analogous compound thereof can be prepared by protecting a nitrogen atom of a compound represented by the above general formula (IId) with an aliphatic acid anhydride represented by the above general formula (XI) in an aliphatic acid such as acetic acid at usually 0° C. to reflux temperature for usually 30 minutes to 1 day, or alternatively, with a succinimide derivative represented by the above general formula (XII) in an inert solvent such as tetrahydrofuran at usually room temperature to reflux temperature for 1 hour to 1 day, and further alternatively, with a reagent for protection represented by the above general formula (XIV) in the presence of a base such as pyridine, triethylamine, N,N-diisopropylethylamine, picoline, lutidine, collidine, quinuclidine, 1,2,2,6,6-pentamethylpiperidine or 1,4-diazabicyclo[2.2.2]octane in an inert solvent such as dichloromethane, acetonitrile, ethyl acetate, diisopropyl ether, chloroform, tetrahydrofuran, 1,2-dimethoxyethane, 1,4-dioxane, acetone, tert-butanol or a mixed solvent thereof, or without any solvent at usually −40° C. to reflux temperature for 30 minutes to 2 days. The reaction time can be appropriately varied based on a used starting material, solvent and reaction temperature.

Process 13

A compound represented by the above general formula (XVI) can be prepared by introducing a hydroxymethyl group into a nitrogen atom of a compound represented by the above general formula (IId) using formaldehyde in a various solvent. As the solvent used in the reaction, water, methanol, ethanol, tetrahydrofuran, dichloromethane, ethyl acetate, N,N-dimethylformamide, acetonitrile, a mixed solvent thereof and the like can be illustrated. The reaction temperature is usually from 0° C. to reflux temperature, and the reaction time is usually from 30 minutes to 1 day, varying based on a used starting material, solvent and reaction temperature.

Process 14

A prodrug represented by the above general formula (IIf) or an analogous compound thereof can be prepared by protecting a hydroxymethyl group of a compound represented by the above general formula (XVI) with a reagent for protection represented by the above general formula (XIV) in the presence of a base such as pyridine, triethylamine, N,N-diisopropylethylamine, picoline, lutidine, collidine, quinuclidine, 1,2,2,6,6-pentamethylpiperidine or 1,4-diazabicyclo[2.2.2]octane in an inert solvent or without any solvent. As the inert solvent used in the reaction, dichloromethane, acetonitrile, ethyl acetate, diisopropyl ether, chloroform, tetrahydrofuran, 1,2-dimethoxyethane, 1,4-dioxane, acetone, tert-butanol, a mixed solvent thereof and the like can be illustrated. The reaction temperature is usually from −40° C. to reflux temperature, and the reaction time is usually from 30 minutes to 2 days, varying based on a used starting material, solvent and reaction temperature.

Process 15

A prodrug represented by the above general formula (IIg) can be prepared by subjecting a compound represented by the above general formula (IIf) to deprotection in the presence of a palladium catalyst such as palladium carbon powder in an inert solvent. As the inert solvent used in the reaction, methanol, ethanol, tetrahydrofuran, ethyl acetate, a mixed solvent thereof and the like can be illustrated. The reaction temperature is usually from 0° C. to reflux temperature, and the reaction time is usually from 30 minutes to 1 day, varying based on a used starting material, solvent and reaction temperature.

Of the compounds represented by the above general formula (III), the following compounds wherein $R^0$ is a phenyl group which may have 1–3 different or same groups selected from a halogen atom and a hydroxy group, or a 5- or 6-membered aromatic heterocyclic group which contains 1–4 different or same atoms selected from an oxygen atom, a sulfur atom and a nitrogen atom in the ring can also be prepared according to the following procedure:

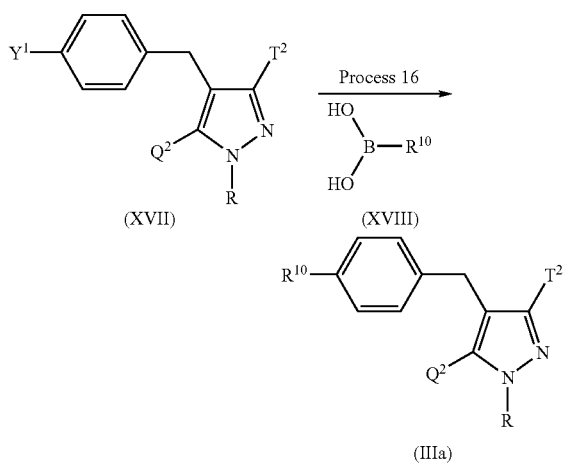

wherein $R^{10}$ represents a phenyl group which may have 1–3 different or same groups selected from a halogen atom and a hydroxy group, or a 5- or 6-membered aromatic heterocyclic group which contains 1–4 different or same atoms selected from an oxygen atom, a sulfur atom and a nitrogen atom in the ring; $Y^1$ represents a leaving group such as a chlorine atom, a bromine atom or an iodine atom; and R, $Q^2$ and $T^2$ have the same meanings as defined above.

Process 16

A compound represented by the above general formula (IIIa) can be prepared by subjecting a glucopyranosyloxypyrazole derivative represented by the above general formula (XVII) that can be prepared using a corresponding starting material in a similar way to the above processes 1 to 3 and 5-1 to Suzuki coupling reaction using a borate compound represented by the above general formula (XVIII) in the presence of a base such as cesium fluoride, sodium carbonate, potassium carbonate, and potassium tert-butoxide, and metal catalyst such as tetrakis(triphenylphosphine)palladium(0), bis(dibenzylidene acetone)palladium (0), bis(triphenylphosphine)palladium(II) dichloride in a various solvent. As the solvent used in the reaction, 1,2-dimethoxyethane, toluene, ethanol, water, a mixed solvent thereof and the like can be illustrated. The reaction temperature is usually from room temperature to reflux temperature, and the reaction time is usually from 1 hour to 1 day, varying based on a used starting material, solvent and reaction temperature.

The glucopyranosyloxypyrazole derivatives represented by the above general formula (I) and the prodrugs thereof of the present invention obtained by the above production processes can be isolated and purified by conventional separation means such as fractional recrystallization, purification using chromatography, solvent extraction and solid phase extraction. Procedures for isolation or purification can be performed occasionally in any production process of glucopyranosyloxypyrazole derivatives represented by the above general formula (I) and prodrugs thereof.

The glucopyranosyloxypyrazole derivatives represented by the above general formula (I) of the present invention and prodrugs thereof can be converted into their pharmaceutically acceptable salts in a usual way. Examples of such salts include acid addition salts with mineral acids such as hydrochloric acid, hydrobromic acid, hydroiodic acid, sulfuric acid, nitric acid, phosphoric acid and the like, acid addition salts with organic acids such as formic acid, acetic acid, adipic acid, citric acid, fumaric acid, maleic acid, oleic acid, lactic acid, stearic acid, succinic acid, tartaric acid, propionic acid, butyric acid, oxalic acid, malonic acid, malic acid, carbonic acid, glutamic acid, aspartic acid, methanesulfonic acid, benzenesulfonic acid, p-toluenesulfonic acid and the like, salts with organic amines such as 2-aminoethanol, piperidine, morpholine, pyrrolidine and the like, and salts with inorganic bases such as a sodium salt, a potassium salt, a calcium salt, a magnesium salt and the like.

The glucopyranosyloxypyrazole derivatives represented by the above general formula (I) of the present invention and prodrugs thereof include their solvates with pharmaceutically acceptable solvents such as ethanol and water.

Among the glucopyranosyloxypyrazole derivatives represented by the above general formula (I) of the present invention and prodrugs thereof, there are two geometrical isomers in each compound having unsaturated bond. In the present invention, either of cis(Z)-isomer or trans(E)-isomer can be employed.

Among the glucopyranosyloxypyrazole derivatives represented by the above general formula (I) of the present invention and prodrugs thereof, there are two optical isomers, R-isomer and S-isomer, in each compound having an asymmetric carbon atom excluding the glucopyranosyloxy moiety. In the present invention, either of R-isomer or S-isomer can be employed, and a mixture of both isomers can be also employed.

The glucopyranosyloxypyrazole derivatives represented by the above general formula (I) of the present invention and prodrugs thereof show an excellent inhibitory activity in human SGLT2. On the other hand, since WAY-123783 has an extremely weak inhibitory activity in human SGLT2, it can not be expected that it exerts an enough effect as a human SGLT2 inhibitor. Therefore, the glucopyranosyloxypyrazole derivatives represented of the present invention and prodrugs thereof are extremely useful as drugs for the prevention or treatment of a disease associated with hyperglycemia such as diabetes, diabetic complications (e.g., retinopathy, neuropathy, nephropathy, ulcer, macroangiopathy), obesity, hyperinsulinemia, glucose metabolism disorder, hyperlipidemia, hypercholesterolemia, hypertriglyceridemia, lipid metabolism disorder, atherosclerosis, hypertension, congestive heart failure, edema, hyperuricemia, gout or the like.

Furthermore, the compounds of the present invention can be suitably used in combination with at least one member selected from drugs other than SGLT2 inhibitors. Examples of the drugs which can be used in combination with the compounds of the present invention include an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor (PDGF), a platelet-derived growth factor (PDGF) analogue (e.g., PDGF-AA, PDGF-BB, PDGF-AB), epidermal growth factor (EGF), nerve growth factor, a carnitine derivative, uridine, 5-hydroxy-1-methylhidantoin, EGB-761, bimoclomol, sulodexide, Y-128, a hydroxymethyl-glutaryl coenzyme A reductase inhibitor, a fibric acid derivative, a $β_3$-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyltransferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an $α_2$-adrenoceptor agonist, an antiplatelets agent, a uric acid synthesis inhibitor, a uricosuric agent and a urinary alkalinizer.

In case of uses of the compound of the present invention in combination with the above one or more drugs, the present invention includes either dosage forms of simultaneous administration as a single preparation or separated preparations in way of same or different administration route, and administration at different dosage intervals as separated preparations in way of same or different administration route. A pharmaceutical combination comprising the compound of the present invention and the above one or more drugs includes both dosage forms as a single preparation and separated preparations for combination as mentioned above.

The compounds of the present invention can obtain more advantageous effects than additive effects in the prevention or treatment of the above diseases when using suitably in combination with the above drugs. Also, the administration dose can be decreased in comparison with administration of either drug alone, or adverse effects of coadministrated drugs other than SGLT2 inhibitors can be avoided or declined.

Concrete compounds as the above drugs used for combination and preferable diseases to be treated are exemplified as follows. However, the present invention is not limited thereto, and for example, the concrete compounds include their free compounds, and their or other pharmaceutically acceptable salts.

As insulin sensitivity enhancers, peroxisome proliferator-activated receptor-γ agonists such as troglitazone, pioglitazone hydrochloride, rosiglitazone maleate, sodium darglitazone, GI-262570, isaglitazone, LG-100641, NC-2100, T-174, DRF-2189, CLX-0921, CS-011, GW-1929, ciglitazone, sodium englitazone and NIP-221, peroxisome proliferator-activated receptor-α agonists such as GW-9578 and BM-170744, peroxisome proliferator-activated receptor-α/γ agonists such as GW-409544, KRP-297, NN-622, CLX-0940, LR-90, SB-219994, DRF-4158 and DRF-MDX8, retinoid X receptor agonists such as ALRT-268, AGN-4204, MX-6054, AGN-194204, LG-100754 and bexarotene, and other insulin sensitivity enhancers such as reglixane, ONO-5816, MBX-102, CRE-1625, FK-614, CLX-0901, CRE-1633, NN-2344, BM-13125, BM-501050, HQL-975, CLX-0900, MBX-668, MBX-675, S-15261, GW-544, AZ-242, LY-510929, AR-H049020 and GW-501516 are illustrated. Insulin sensitivity enhancers are used preferably for diabetes, diabetic complications, obesity, hyperinsulinemia, glucose metabolism disorder, hyperlipidemia, hypercholesterolemia, hypertriglyceridemia, lipid metabolism disorder or atherosclerosis, and more preferably for diabetes, hyperinsulinemia or glucose metabolism disorder because of improving the disturbance of insulin signal transduction in peripheral tissues and enhancing glucose uptake into the tissues from the blood, leading to lowering blood glucose level.

As glucose absorption inhibitors, α-glucosidase inhibitors such as acarbose, voglibose, miglitol, CKD-711, emiglitate, MDL-25,637, camiglibose and MDL-73,945, and α-amylase inhibitors such as AZM-127 are illustrated. Glucose absorption inhibitors are used preferably for diabetes, diabetic complications, obesity, hyperinsulinemia or glucose metabolism disorder, and more preferably for diabetes or glucose metabolism disorder because of inhibiting the gastrointestinal enzymatic digestion of carbohydrates contained in foods, and inhibiting or delaying the absorption of glucose into the body.

As biguanides, phenformin, buformin hydrochloride, metformin hydrochloride and the like are illustrated. Biguanides are used preferably for diabetes, diabetic complications, hyperinsulinemia or glucose metabolism disorder, and more preferably for diabetes, hyperinsulinemia or glucose metabolism disorder because of lowering blood glucose level by inhibitory effects on hepatic gluconeogenesis, accelerating effects on anaerobic glycolysis in tissues or improving effects on insulin resistance in peripheral tissues.

As insulin secretion enhancers, tolbutamide, chlorpropamide, tolazamide, acetohexamide, glyclopyramide, glyburide (glibenclamide), gliclazide, 1-butyl-3-metanilylurea, carbutamide, glibornuride, glipizide, gliquidone, glisoxapide, glybuthiazol, glybuzole, glyhexamide, sodium glymidine, glypinamide, phenbutamide, tolcyclamide, glimepiride, nateglinide, mitiglinide calcium hydrate, repaglinide and the like are illustrated. Insulin secretion enhancers are used preferably for diabetes, diabetic complications or glucose metabolism disorder, and more preferably for diabetes or glucose metabolism disorder because of lowering blood glucose level by acting on pancreatic β-cells and enhancing the insulin secretion.

As insulin preparations, human insulin, human insulin analogues, animal-deprived insulin and the like are illustrated. Insulin preparations are used preferably for diabetes, diabetic complications or glucose metabolism disorder, and more preferably for diabetes or glucose metabolism disorder.

As glucagon receptor antagonists, BAY-27-9955, NNC-92-1687 and the like are illustrated; as insulin receptor kinase stimulants, TER-17411, L-783281, KRX-613 and the like are illustrated; as tripeptidyl peptidase II inhibitors, UCL-1397 and the like are illustrated; as dipeptidyl peptidase IV inhibitors, NVP-DPP728A, TSL-225, P-32/98 and the like are illustrated; as protein tyrosine phosphatase 1B inhibitors, PTP-112, OC-86839, PNU-177496 and the like are illustrated; as glycogen phosphorylase inhibitors, NN-4201, CP-368296 and the like are illustrated; as fructose-bisphosphatase inhibitors, R-132917 and the like are illustrated; as pyruvate dehydrogenase inhibitors, AZD-7545 and the like are illustrated; as hepatic gluconeogenesis inhibitors, FR-225659 and the like are illustrated; as glucagon-like peptide-1 analogues, exendin-4, CJC-1131 and the like are illustrated; as glucagon-like peptide 1 agonists; AZM-134, LY-315902 and the like are illustrated; and as amylin, amylin analogues or amylin agonists, pramlintide acetate and the like are illustrated. These drugs, glucose-6-phosphatase inhibitors, D-chiroinsitol, glycogen synthase kinase-3 inhibitors, glucagon-like peptide-1 are used preferably for diabetes, diabetic complications, hyperinsulinemia or glucose metabolism disorder, and more preferably for diabetes or glucose metabolism disorder.

As aldose reductase inhibitors, ascorbyl gamolenate, tolrestat, epalrestat, ADN-138, BAL-ARI8, ZD-5522, ADN-311, GP-1447, IDD-598, fidarestat, sorbinil, ponalrestat, risarestat, zenarestat, minalrestat, methosorbinil, AL-1567, imirestat, M-16209, TAT, AD-5467, zopolrestat, AS-3201, NZ-314, SG-210, JTT-811, lindolrestat and the like are illustrated. Aldose reductase inhibitors are preferably used for diabetic complications because of inhibiting aldose reductase and lowering excessive intracellular accumulation of sorbitol in accelerated polyol pathway which are in continuous hyperglycemic condition in the tissues in diabetic complications.

As advanced glycation endproducts formation inhibitors, pyridoxamine, OPB-9195, ALT-946, ALT-711, pimagedine hydrochloride and the like are illustrated. Advanced glycation endproducts formation inhibitors are preferably used for diabetic complications because of inhibiting formation of advanced glycation endproducts which are accelerated in continuous hyperglycemic condition in diabetes and declining cellular damage.

As protein kinase C inhibitors, LY-333531, midostaurin and the like are illustrated. Protein kinase C inhibitors are preferably used for diabetic complications because of inhibiting protein kinase C activity which is accelerated in continuous hyperglycemic condition in diabetes.

As γ-aminobutyric acid receptor antagonists, topiramate and the like are illustrated; as sodium channel antagonists, mexiletine hydrochloride, oxcarbazepine and the like are illustrated; as transcrit factor NF-κB inhibitors, dexlipotam and the like are illustrated; as lipid peroxidase inhibitors, tirilazad mesylate and the like are illustrated; as N-acetylated-α-linked-acid-dipeptidase inhibitors, GPI-5693 and the like are illustrated; and as carnitine derivatives, carnitine, levacecarnine hydrochloride, levocarnitine chloride, levocarnitine, ST-261 and the like are illustrated. These drugs, insulin-like growth factor-I, platelet-derived growth factor, platelet derived growth factor analogues, epidermal growth factor, nerve growth factor, uridine, 5-hydroxy-1-methylhidantoin, EGB-761, bimoclomol, sulodexide and Y-128 are preferably used for diabetic complications.

As hydroxymethylglutaryl coenzyme A reductase inhibitors, sodium cerivastatin, sodium pravastatin, lovastatin, simvastatin, sodium fluvastatin, atorvastatin calcium hydrate, SC-45355, SQ-33600, CP-83101, BB-476, L-669262, S-2468, DMP-565, U-20685, BAY-x-2678, BAY-10-2987, calcium pitavastatin, calcium rosuvastatin, colestolone, dalvastatin, acitemate, mevastatin, crilvastatin, BMS-180431, BMY-21950, glenvastatin, carvastatin, BMY-22089, bervastatin and the like are illustrated. Hydroxymethylglutaryl coenzyme A reductase inhibitors are used preferably for hyperlipidemia, hypercholesterolemia, hypertriglyceridemia, lipid metabolism disorder or atherosclerosis, and more preferably for hyperlipidemia, hypercholesterolemia or atherosclerosis because of lowering blood cholesterol level by inhibiting hydroxymethylglutaryl coenzyme A reductase.

As fibric acid derivatives, bezafibrate, beclobrate, binifibrate, ciprofibrate, clinofibrate, clofibrate, aluminum clofibrate, clofibric acid, etofibrate, fenofibrate, gemfibrozil, nicofibrate, pirifibrate, ronifibrate, simfibrate, theofibrate, AHL-157 and the like are illustrated. Fibric acid derivatives are used preferably for hyperinsulinemia, hyperlipidemia, hypercholesterolemia, hypertriglyceridemia, lipid metabolism disorder or atherosclerosis, and more preferably for hyperlipidemia, hypertriglyceridemia or atherosclerosis because of activating hepatic lipoprotein lipase and enhancing fatty acid oxidation, leading to lowering blood triglyceride level.

As $\beta_3$-adrenoceptor agonists, BRL-28410, SR-58611A, ICI-198157, ZD-2079, BMS-194449, BRL-37344, CP-331679, CP-114271, L-750355, BMS-187413, SR-59062A, BMS-210285, LY-377604, SWR-0342SA, AZ-40140, SB-226552, D-7114, BRL-35135, FR-149175, BRL-26830A, CL-316243, AJ-9677, GW-427353, N-5984, GW-2696 and the like are illustrated. $\beta_3$-Adrenoceptor agonists are used preferably for obesity, hyperinsulinemia, hyperlipidemia, hypercholesterolemia, hypertriglyceridemia or lipid metabolism disorder, and more preferably for obesity or hyperinsulinemia because of stimulating $\beta_3$-adrenoceptor in adipose tissue and enhancing the fatty acid oxidation, leading to induction of energy expenditure.

As acyl-coenzyme A cholesterol acyltransferase inhibitors, NTE-122, MCC-147, PD-132301-2, DUP-129, U-73482, U-76807, RP-70676, P-06139, CP-113818, RP-73163, FR-129169, FY-038, EAB-309, KY-455, LS-3115, FR-145237, T-2591, J-104127, R-755, FCE-28654, YIC-C8-434, avasimibe, CI-976, RP-64477, F-1394, eldacimibe, CS-505, CL-283546, YM-17E, lecimibide, 447C88, YM-750, E-5324, KW-3033, HL-004, eflucimibe and the like are illustrated. Acyl-coenzyme A cholesterol acyltransferase inhibitors are used preferably for hyperlipidemia, hypercholesterolemia, hypertriglyceridemia or lipid metabolism disorder, and more preferably for hyperlipidemia or hypercholesterolemia because of lowering blood cholesterol level by inhibiting acyl-coenzyme A cholesterol acyltransferase.

As thyroid hormone receptor agonists, sodium liothyronine, sodium levothyroxine, KB-2611 and the like are illustrated; as cholesterol absorption inhibitors, ezetimibe, SCH-48461 and the like are illustrated; as lipase inhibitors, orlistat, ATL-962, AZM-131, RED-103004 and the like are illustrated; as carnitine palmitoyltransferase inhibitors, etomoxir and the like are illustrated; as squalene synthase inhibitors, SDZ-268-198, BMS-188494, A-87049, RPR-101821, ZD-9720, RPR-107393, ER-27856 and the like are illustrated; as nicotinic acid derivatives, nicotinic acid, nicotinamide, nicomol, niceritrol, acipimox, nicorandil and the like are illustrated; as bile acid sequestrants, colestyramine, colestilan, colesevelam hydrochloride, GT-102-279 and the like are illustrated; as sodium/bile acid cotransporter inhibitors, 264W94, S-8921, SD-5613 and the like are illustrated; and as cholesterol ester transfer protein inhibitors, PNU-107368E, SC-795, JTT-705, CP-529414 and the like are illustrated. These drugs, probcol, microsomal triglyceride transfer protein inhibitors, lipoxygenase inhibitors and low-density lipoprotein receptor enhancers are preferably used for hyperlipidemia, hypercholesterolemia, hypertriglyceridemia or lipid metabolism disorder.

As appetite suppressants, monoamine reuptake inhibitors, serotonin reuptake inhibitors, serotonin releasing stimulants, serotonin agonists (especially $5HT_{2C}$-agonists), noradrenalin reuptake inhibitors, noradrenalin releasing stimulants, $\alpha_1$-adrenoceptor agonists, $\beta_2$-adrenoceptor agonists, dopamine agonists, cannabinoid receptor antagonists, $\gamma$-aminobutyric acid receptor antagonists, $H_3$-histamine antagonists, L-histidine, leptin, leptin analogues, leptin receptor agonists, melanocortin receptor agonists (especially, MC3-R agonists, MC4-R agonists), $\alpha$-melanocyte stimulating hormone, cocaine- and amphetamine-regulated transcript, mahogany protein, enterostatin agonists, calcitonin, calcitonin-gene-related peptide, bombesin, cholecystokinin agonists (especially CCK-A agonists), corticotropin-releasing hormone, corticotrophin-releasing hormone analogues, corticotropin-releasing hormone agonists, urocortin, somatostatin, somatostatin analogues, somatostatin receptor agonists, pituitary adenylate cyclase-activating peptide, brain-derived neurotrophic factor, ciliary neurotrophic factor, thyrotropin-releasing hormone, neurotensin, sauvagine, neuropeptide Y antagonists, opioid peptide antagonists, galanin antagonists, melanin-concentrating hormone antagonists, agouti-related protein inhibitors and orexin receptor antagonists are illustrated. Concretely, as monoamine reuptake inhibitors, mazindol and the like are illustrated; as serotonin reuptake inhibitors, dexfenfluramine hydrochloride, fenfluramine, sibutramine hydrochloride, fluvoxamine maleate, sertraline hydrochloride and the like are illustrated; as serotonin agonists, inotriptan, (+)-norfenfluramine and the like are illustrated; as noradrenaline reuptake inhibitors, bupropion, GW-320659 and the like are illustrated; as noradrenaline releasing stimulants, rolipram, YM-992 and the like are illustrated; as $\beta_2$-adrenoceptor agonists, amphetamine, dextroamphetamine, phentermine, benzphetamine, methamphetamine, phendimetrazine, phenmetrazine, diethylpropion, phenylpropanolamine, clobenzorex and the like are illustrated; as dopamine agonists, ER-230, doprexin, bromocriptine mesylate and the like are illustrated; as cannabinoid receptor antagonists, rimonabant and the like are illustrated; as $\gamma$-aminobutyric acid receptor antagonists, topiramate and the like are illustrated; as $H_3$-histamine antagonists, GT-2394 and the like are illustrated; as leptin, leptin analogues or leptin receptor agonists, LY-355101 and the like are illustrated; as cholecystokinin agonists (especially CCK-A agonists), SR-146131, SSR-125180, BP-3.200, A-71623, FPL-15849, GI-248573, GW-7178, GI-181771, GW-7854, A-71378 and the like are illustrated; and as neuropeptide Y antagonists, SR-120819-A, PD-160170, NGD-95-1, BIBP-3226, 1229-U-91, CGP-71683, BIBO-3304, CP-671906-01, J-115814 and the like are illustrated. Appetite suppressants are used preferably for diabetes, diabetic complications, obesity, glucose metabolism disorder, hyperlipidemia, hypercholesterolemia, hypertriglyceridemia, lipid metabolism disorder, atherosclerosis, hypertension, congestive heart failure, edema, hyperuricemia or gout, and more preferably for obesity because of stimulating or inhibiting the activities of intracerebral monoamines or bioactive peptides in central appetite regulatory system and suppressing the appetite, leading to reduction of energy intake.

As angiotensin-converting enzyme inhibitors, captopril, enalapri maleate, alacepril, delapril hydrochloride, ramipril, lisinopril, imidapril hydrochloride, benazepril hydrochloride, ceronapril monohydrate, cilazapril, sodium fosinopril, perindopril erbumine, calcium moveltipril, quinapril hydrochloride, spirapril hydrochloride, temocapril hydrochloride, trandolapril, calcium zofenopril, moexipril hydrochloride, rentiapril and the like are illustrated. Angiotensin-converting enzyme inhibitors are preferably used for diabetic complications or hypertension.

As neutral endopeptidase inhibitors, omapatrilat, MDL-100240, fasidotril, sampatrilat, GW-660511X, mixanpril, SA-7060, E-4030, SLV-306, ecadotril and the like are illustrated. Neutral endopeptidase inhibitors are preferably used for diabetic complications or hypertension.

As angiotensin II receptor antagonists, candesartan cilexetil, candesartan cilexetil/hydrochlorothiazide, potassium losartan, eprosartan mesylate, valsartan, telmisartan, irbesartan, EXP-3174, L-158809, EXP-3312, olmesartan, tasosartan, KT-3-671, GA-0113, RU-64276, EMD-90423, BR-9701 and the like are illustrated. Angiotensin II receptor antagonists are preferably used for diabetic complications or hypertension.

As endothelin-converting enzyme inhibitors, CGS-31447, CGS-35066, SM-19712 and the like are illustrated; as endothelin receptor antagonists, L-749805, TBC-3214, BMS-182874, BQ-610, TA-0201, SB-215355, PD-180988, sodium sitaxsentan, BMS-193884, darusentan, TBC-3711, bosentan, sodium tezosentan, J-104132, YM-598, S-0139, SB-234551, RPR-118031A, ATZ-1993, RO-61-1790, ABT-546, enlasentan, BMS-207940 and the like are illustrated. These drugs are preferably used for diabetic complications or hypertension, and more preferably for hypertension.

As diuretic agents, chlorthalidone, metolazone, cyclopenthiazide, trichloromethiazide, hydrochlorothiazide, hydroflumethiazide, benzylhydrochlorothiazide, penflutizide, methyclothiazide, indapamide, tripamide, mefruside, azosemide, etacrynic acid, torasemide, piretanide, furosemide, bumetanide, meticrane, potassium canrenoate, spironolactone, triamterene, aminophylline, cicletanine hydrochloride, LLU-$\alpha$, PNU-80873A, isosorbide, D-mannitol, D-sorbitol, fructose, glycerin, acetazolamide, methazolamide, FR-179544, OPC-31260, lixivaptan, conivaptan hydrochloride and the like are illustrated. Diuretic drugs are preferably used for diabetic complications, hypertension, congestive heart failure or edema, and more preferably for hypertension, congestive heart failure or edema because of reducing blood pressure or improving edema by increasing urinary excretion.

As calcium antagonists, aranidipine, efonidipine hydrochloride, nicardipine hydrochloride, barnidipine hydrochloride, benidipine hydrochloride, manidipine hydrochloride, cilnidipine, nisoldipine, nitrendipine, nifedipine, nilvadipine, felodipine, amlodipine besilate, pranidipine, lercanidipine hydrochloride, isradipine, elgodipine, azelnidipine, lacidipine, vatanidipine hydrochloride, lemildipine, diltiazem hydrochloride, clentiazem maleate, verapamil hydrochloride, S-verapamil, fasudil hydrochloride, bepridil hydrochloride, gallopamil hydrochloride and the like are illustrated; as vasodilating antihypertensive agents, indapamide, todralazine hydrochloride, hydralazine hydrochloride, cadralazine, budralazine and the like are illustrated; as sympathetic blocking agents, amosulalol hydrochloride, terazosin hydrochloride, bunazosin hydrochloride, prazosin hydrochloride, doxazosin mesylate, propranolol hydrochloride, atenolol, metoprolol tartrate, carvedilol, nipradilol, celiprolol hydrochloride, nebivolol, betaxolol hydrochloride, pindolol, tertatolol hydrochloride, bevantolol hydrochloride, timolol maleate, carteolol hydrochloride, bisoprolol hemifumarate, bopindolol malonate, nipradilol, penbutolol sulfate, acebutolol hydrochloride, tilisolol hydrochloride, nadolol, urapidil, indoramin and the like are illustrated; as centrally acting antihypertensive agents, reserpine and the like are illustrated; and as $\alpha_2$-adrenoceptor agonists, clonidine hydrochloride, methyldopa, CHF-1035, guanabenz acetate, guanfacine hydrochloride, moxonidine, lofexidine, talipexole hydrochloride and the like are illustrated. These drugs are preferably used for hypertension.

As antiplatelets agents, ticlopidine hydrochloride, dipyridamole, cilostazol, ethyl icosapentate, sarpogrelate hydrochloride, dilazep dihydrochloride, trapidil, beraprost sodium, aspirin and the like are illustrated. Antiplatelets agents are preferably used for atherosclerosis or congestive heart failure.

As uric acid synthesis inhibitors, allopurinol, oxypurinol and the like are illustrated; as uricosuric agents, benzbromarone, probenecid and the like are illustrated; and as urinary alkalinizers, sodium hydrogen carbonate, potassium citrate, sodium citrate and the like are illustrated. These drugs are preferably used for hyperuricemia or gout.

In case of use in combination with drugs other than SGLT2 inhibitors, for example, in the use for diabetes, the combination with at least one member of the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist and an appetite suppressant is preferable; the combination with at least one member of the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue and an amylin agonist is more preferable; and the combination with at least one member of the group consisting of an insulin sensitivity enhancer, a glucose absorption inhibitor, a biguanide, an insulin secretion enhancer and an insulin preparation is most preferable. Similarly, in the use for diabetic complications, the combination with at least one member of the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, glycogen synthase kinase-3 inhibitors, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet derived growth factor analogue, epidermal growth factor, nerve growth factor, a carnitine derivative, uridine, 5-hydroxy-1-methylhidantoin, EGB-761, bimoclomol, sulodexide, Y-128, an angiotensin-converting enzyme inhibitor, a neutral endopeptidase inhibitor, an angiotensin II receptor antagonist, an endothelin-converting enzyme inhibitor, an endothelin receptor antagonist and a diuretic agent is preferable; and the combination with at least one member of the group consisting of an aldose reductase inhibitor, an angiotensin-converting enzyme inhibitor, a neutral endopeptidase inhibitor and an angiotensin II receptor antagonist is more preferable. Furthermore, in the use for obesity, the combination with at least one member of the group consisting of an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, a $\beta_3$-adrenoceptor agonist and an appetite suppressant is preferable; and the combination with at least one member of the group consisting of a $\beta_3$-adrenoceptor agonist and an appetite suppressant is more preferable.

When the pharmaceutical compositions of the present invention are employed in the practical treatment, various dosage forms are used depending on their uses. As examples of the dosage forms, powders, granules, fine granules, dry syrups, tablets, capsules, injections, solutions, ointments, suppositories, poultices and the like are illustrated, which are orally or parenterally administered.

These pharmaceutical compositions can be prepared by admixing with or by diluting and dissolving an appropriate pharmaceutical additive such as excipients, disintegrators, binders, lubricants, diluents, buffers, isotonicities, antiseptics, moistening agents, emulsifiers, dispersing agents, stabilizing agents, dissolving aids and the like, and formulating the mixture in accordance with pharmaceutically conventional methods depending on their dosage forms. In case of the use of the compound of the present invention in combination with the drugs other than SGLT2 inhibitors, they can be prepared by formulating each active ingredient together or individually.

When the pharmaceutical compositions of the present invention are employed in the practical treatment, the dosage of a compound represented by the above general formula (I), a pharmaceutically acceptable salt thereof or a prodrug thereof as the active ingredient is appropriately decided depending on the age, sex, body weight and degree of symptoms and treatment of each patient, which is approximately within the range of from 0.1 to 1,000 mg per day per adult human in the case of oral administration and approximately within the range of from 0.01 to 300 mg per day per adult human in the case of parenteral administration, and the daily dose can be divided into one to several doses per day and administered suitably. Also, in case of the use of the compound of the present invention in combination with the drugs other than SGLT2 inhibitors, the dosage of the compound of the present invention can be decreased depending on the dosage of the drugs other than SGLT2 inhibitors.

The present invention is further illustrated in more detail by way of the following Reference Examples, Examples and Test Examples. However, the present invention is not limited thereto.

REFERENCE EXAMPLE 1

Methyl 4-(cyclopropylidenemethyl)benzoate

To a suspension of sodium hydride (60%, 0.27 g) in tetrahydrofuran (40 mL) was added cyclopropyltriphenylphosphonium bromide (2.6 g), and the mixture was stirred at 70° C. for 2 hours. To the reaction mixture was added methyl terephthalaldehydate (1.0 g), and the mixture was stirred at 70° C. for 7 days. Water was added to the reaction mixture, and the mixture was extracted with diethyl ether. The organic layer was washed with water and brine, and dried over anhydrous magnesium sulfate, and the solvent was removed under reduced pressure. The residue was purified by column chromatography on silica gel (eluent: hexane/dichloromethane=1/1) to give methyl 4-(cyclopropylidenemethyl)benzoate (0.80 g).

$^1$H-NMR (CDCl$_3$) δ ppm: 1.15–1.30 (2H, m), 1.40–1.50 (2H, m), 3.91 (3H, s), (1H, m), 7.55–7.60 (2H, m), 7.95–8.05 (2H, m)

REFERENCE EXAMPLE 2

4-(Cyclopropylidenemethyl)benzyl alcohol

To a suspension of lithium aluminum hydride (0.16 g) in tetrahydrofuran (30 mL) was added methyl 4-(cyclopropylidenemethyl)benzoate (0.80 g), and the mixture was stirred at room temperature for 5 hours. Water (0.4 mL) was added to the reaction mixture, and the mixture was stirred for 3 days. Insoluble materials were removed by filtration, and the solvent of the filtrate was removed under reduced pressure to give 4-(cyclopropylidenemethyl)benzyl alcohol (0.69 g).

$^1$H-NMR (CDCl$_3$) δ ppm: 1.15–1.25 (2H, m), 1.35–1.50 (2H, m), 1.61 (1H, t, J=6.0Hz), 4.68 (2H, d, J=6.0 Hz), 6.70–6.80 (1H, m), 7.30–7.35 (2H, m), 7.50–7.55 (2H, m)

EXAMPLE 1

5-Methyl-4-{[4-(cyclopropylidenemethyl)phenyl]methyl}-1,2-dihydro-3H-pyrazol-3-one To a solution of 4-(cyclopropylidenemethyl)benzyl alcohol (0.21 g) and triethylamine (0.18 mL) in tetrahydrofuran was added methanesulfonyl chloride (0.10 mL), and the mixture was stirred at room temperature for 30 minutes. Insoluble materials were removed by filtration. A solution of the obtained 4-(cyclopropylidenemethyl)benzyl methanesulfonate in tetrahydrofuran was added to a suspension of sodium hydride (60%, 0.052 g) and methyl acetoacetate (0.14 mL) in 1,2-dimethoxyethane, and the mixture was stirred at 70° C. for 5 hours. To the reaction mixture was added a saturated aqueous sodium hydrogen carbonate solution, and the mixture was extracted with diethyl ether. The organic layer was dried over anhydrous magnesium sulfate, and the solvent was removed under reduced pressure. To a solution of the residue in toluene was added anhydrous hydrazine (0.12 mL), and the mixture was stirred at 95° C. for 10 minutes. The solvent of the reaction mixture was removed under reduced pressure, and the residue was purified by column chromatography on silica gel (eluent: dichloromethane/methanol=10/1) to give 5-methyl-4-{[4-(cyclopropylidenemethyl)phenyl]methyl}-1,2-dihydro-3H-pyrazol-3-one (0.032 g).

$^1$H-NMR (DMSO-d$_6$) δ ppm: 1.10–1.20 (2H, m), 1.30–1.45 (2H, m), 2.00 (3H, s), 3.52 (2H, s), 6.65–6.75 (1H, m), 7.05–7.15 (2H, m), 7.35–7.45 (2H, m)

EXAMPLE 2

5-Methyl-4-{[4-(cyclopropylidenemethyl)phenyl]methyl}-3-(2,3,4,6-tetra-O-acetyl-β-D-glucopyranosyloxy)-1H-pyrazole To a suspension of 5-methyl-4-{[4-(cyclopropylidenemethyl)phenyl]methyl}-1,2-dihydro-3H-pyrazol-3-one (0.026 g) and acetobromo-α-D-glucose (0.049 g) in tetrahydrofuran was added silver carbonate (0.036 g), and the mixture was stirred at 60° C. overnight under light shielding. The reaction mixture was purified by column chromatography on aminopropyl silica gel (eluent: tetrahydrofuran) and successively by column chromatography on silica gel (eluent: hexane/ethyl acetate=1/3) to give 5-methyl-4-{[4-(cyclopropylidenemethyl)phenyl]methyl}-3-(2,3,4,6-tetra-O-acetyl-β-D-glucopyranosyloxy)-1H-pyrazole (0.010 g).

$^1$H-NMR (CDCl$_3$) δ ppm: 1.10–1.20 (2H, m), 1.30–1.45 (2H, m), 1.86 (3H, s), 2.03 (3H, s), 2.06 (3H, s), 2.11 (3H, s), 3.50–3.70 (2H, m), 3.80–3.90 (1H, m), 4.13 (1H, dd, J=2.3, 12.4 Hz), 4.31 (1H, dd, J=4.1, 12.4 Hz), 5.15–5.35 (3H, m), 5.50–5.65 (1H, m), 6.65–6.75 (1H, m), 7.05–7.15 (2H, m), 7.35–7.45 (2H, m)

REFERENCE EXAMPLE 3

4-Cyclopropylbenzaldehyde

To a solution of 4-bromostylene (1.83 g) in dichloromethane (5 mL) was added diethylzinc (1 mol/L, 30 mL) under an argon atmosphere at 0° C., and the mixture was stirred at the same temperature for 10 minutes. Chloroiodomethane (4.3 mL) was added to the mixture, and the mixture was warmed to room temperature and stirred for 9 days. To the reaction mixture was added a saturated aqueous ammonium chloride solution, and the mixture was extracted with diethyl ether. The organic layer was dried over anhydrous sodium sulfate, and the solvent was removed under reduced pressure to give 4-cyclopropylbromobenzene. The obtained 4-cyclopropylbromobenzene was dissolved in tetrahydrofuran (25 mL) and cooled to −78° C. To the solution was added dropwise tert-butyl lithium (1.45 mol/L pentane solution, 9.4 mL) under an argon atmosphere, and the mixture was stirred at −78° C. for 30 minutes. To the reaction mixture was added a solution of N,N-dimethylformamide (1.2 mL) in tetrahydrofuran (16 mL), and the mixture was warmed to 0° C. and stirred for 1 hour. To the reaction mixture was added a saturated aqueous ammonium chloride solution, and the mixture was extracted with diethyl ether. The organic layer was dried over anhydrous sodium sulfate, and the solvent was removed under reduced pressure. The residue was purified by column chromatography on silica gel (eluent: hexane/ethyl acetate=12/1) to give 4-cyclopropylbenzaldehyde (0.72 g).

$^1$H-NMR (CDCl$_3$) δ ppm: 0.60–0.75 (2H, m), 1.05–1.15 (2H, m), 1.80–1.95 (1H, m), 7.15–7.25 (2H, m), 7.70–7.80 (2H, m), 9.94 (1H, s)

REFERENCE EXAMPLE 4

4-Cyclopropylbenzyl alcohol

To a solution of 4-cyclopropylbenzaldehyde (0.71 g) in methanol (10 mL) was added lithium borohydride (2 mol/L tetrahydrofuran solution, 3.7 mL), and the mixture was warmed to room temperature and stirred for 30 minutes. To the reaction mixture was added water, and the mixture was extracted with diethyl ether. The organic layer was washed with 1 mol/L hydrochloric acid solution and brine, and dried over anhydrous sodium sulfate. The solvent was removed under reduced pressure, and the residue was purified by column chromatography on silica gel (eluent: hexane/ethyl acetate=5/1) to give 4-cyclopropylbenzyl alcohol (0.69 g).

$^1$H-NMR (CDCl$_3$) δ ppm: 0.60–0.75 (2H, m), 0.90–1.00 (2H, m), 1.80–1.95 (1H, m), 4.62 (2H, s), 7.00–7.10 (2H, m), 7.20–7.30 (2H, m)

EXAMPLE 3

5-Methyl-4-[(4-cyclopropylphenyl)methyl]-1,2-dihydro-3H-pyrazol-3-one

To a solution of 4-cyclopropylbenzyl alcohol (1.1 g) in tetrahydrofuran (23 mL) were added triethylamine (1.2 mL) and methanesulfonyl chloride (0.66 mL), and the mixture was stirred at room temperature for 2 hours. Insoluble materials were removed by filtration. A solution of the obtained 4-cyclopropylbenzyl methanesulfonate in tetrahydrofuran was added to a suspension of sodium hydride (60%, 0.34 g) and methyl acetoacetate (0.91 mL) in 1,2-dimethoxyethane (26 mL), and the mixture was stirred at 80° C. for 13 hours. Into the reaction mixture was poured a saturated aqueous sodium hydrogen carbonate solution, and the mixture was extracted with diethyl ether. The organic layer was dried over anhydrous sodium sulfate, and the solvent was removed under reduced pressure. The residue was dissolved in toluene (23 mL), to the solution was added hydrazine monohydrate (1.1 mL), and the mixture was stirred at 100° C. for 10 hours. After cooling to room temperature, resulting insoluble materials was collected by filtration, washed with water and then hexane and dried under reduced pressure to give 5-methyl-4-[(4-cyclopropylphenyl)methyl]-1,2-dihydro-3H-pyrazol-3-one (1.22 g).

$^1$H-NMR (CD$_3$OD) δ ppm: 0.50–0.65 (2H, m), 0.80–0.95 (2H, m), 1.75–1.90 (1H, m), 2.01 (3H, s), 3.58 (2H, s), 6.85–7.10 (4H, m)

EXAMPLE 4

5-Methyl-4-[(4-cyclopropylphenyl)methyl]-3-(2,3,4,6-tetra-O-acetyl-β-D-glucopyranosyloxy)-1H-pyrazole To a suspension of 5-methyl-4-[(4-cyclopropylphenyl)methyl]-1,2-dhydro-3H-pyrazol-3-one (0.23 g) and acetobromo-α-D-glucose (0.45 g) in tetrahydrofuran (5 mL) was added silver carbonate (0.33 g), and the mixture was stirred at 40° C. for 36 hours under light shielding. The reaction mixture was purified by column chromatography on aminopropyl silica gel (eluent: tetrahydrofuran) and successively by column chromatography on silica gel (eluent: hexane/ethyl acetate=1/2) to give 5-methyl-4-[(4-cyclopropylphenyl)methyl]-3-(2,3,4,6-tetra-O-acetyl-β-D-glucopyranosyloxy)-1H-pyrazole (0.30 g).

$^1$H-NMR (CDCl$_3$) δ ppm: 0.55–0.70 (2H, m), 0.85–1.00 (2H, m), 1.75–1.90 (1H, m), 1.86 (3H, s), 2.01 (3H, s), 2.03 (3H, s), 2.06 (3H, s), 2.10 (3H, s), 3.54 (1H, d, J=15.8 Hz), 3.61 (1H, d, J=15.8 Hz), 3.80–3.90 (1H, m), 4.12 (1H, dd, J=2.3, 12.4 Hz), 4.30 (1H, dd, J=4.1, 12.4 Hz), 5.15–5.35 (3H, m), 5.50–5.65 (1H, m), 6.85–7.05 (4H, m)

REFERENCE EXAMPLE 5

Methyl (E)-4-(but-1-en-1-yl)benzoate

To a suspension of sodium hydride (60%, 0.97 g) in tetrahydrofuran (80 mL) was added methyl 4-(diethylphosphorylmethyl)benzoate (5.8 g) at 0° C., and the mixture was stirred for 30 minutes. To the reaction mixture was added a solution of propionaldehyde (1.6 mL) in tetrahydrofuran (10 mL), and the mixture was stirred at room temperature for 30 minutes. To the reaction mixture was added a saturated aqueous ammonium chloride solution, and the mixture was extracted with diethyl ether. The organic layer was washed with water and dried over anhydrous magnesium sulfate, and the solvent was removed under reduced pressure. The residue was purified by column chromatography on silica gel (eluent: hexane/ethyl acetate=5/1) to give methyl (E)-4-(but-1-en-1-yl)benzoate (2.5 g).

$^1$H-NMR (CDCl$_3$) δ ppm: 1.11 (3H, t, J=7.5 Hz), 2.20–2.35 (2H, m), 3.90 (3H, s), 6.35–6.45) (2H, m), 7.35–7.45 (2H, m), 7.90–8.00 (2H, m)

REFERENCE EXAMPLE 6

(E)-4-(But-1-en-1-yl)benzyl alcohol

To a suspension of lithium aluminum hydride (1.2 g) in diethyl ether (100 mL) was added a solution of methyl 4-(but-1-en-1-yl)benzoate (2.5 g) in diethyl ether (20 mL) at 0° C., and the mixture was heated under reflux for 30 mixture. After the reaction mixture was cooled to 0° C., to the mixture were added water (1.2 mL), an aqueous sodium hydroxide solution (15%, 1.2 mL) and water (3.6 mL), and the mixture was stirred at room temperature for 5 minutes. Insoluble materials were removed by filtration, and the filtrate was concentrated under reduced pressure. The residue was purified by column chromatography on silica gel (eluent: hexane/ethyl acetate=2/1) to give (E)-4-(but-1-en-1-yl)benzyl alcohol (1.9 g).

$^1$H-NMR (CDCl$_3$) δ ppm: 1.09 (3H, t, J=7.5 Hz), 1.60 (1H, t, J=6.0 Hz), 2.15–2.30 (2H, m), 4.66 (2H, d, J=6.0 Hz), 6.27 (1H, dt, J=15.9, 6.3 Hz), 6.37 (1H, d, J=15.9 Hz), 7.25–7.40 (4H, m)

EXAMPLE 5

(E)-4-{[4-(But-1-en-1-yl)phenyl]methyl}-5-methyl-1,2-dihydro-3H-pyrazol-3-one The title compound was prepared in a similar manner to that described in Example 3 using 4-(but-1-en-1-yl)benzyl alcohol instead of 4-cyclopropylbenzyl alcohol.

$^1$H-NMR (DMSO-d$_6$) δ ppm: 1.03 (3H, t, J=7.5 Hz), 1.99 (3H, s), 2.10–2.25 (2H, m), 3.51 (2H, s), 6.23 (1H, dt, J=16.0, 6.2 Hz), 6.32 (1H, d, J=16.0 Hz), 7.05–7.10 (2H, m), 7.20–7.30 (2H, m)

EXAMPLE 6

(E)-4-{[4-(But-1-en-1-yl)phenyl]methyl}-5-methyl-3-(2,3,4,6-tetra-O-acetyl-β-D-glucopyranosyloxy)-1H-pyrazole The title compound was prepared in a similar manner to that described in Example 4 using (E)-4-{[4-(but-1-en-1-yl)phenyl]methyl}-5-methyl-1,2-dihydro-3H-pyrazol-3-one instead of 5-methyl-4-[(4-cyclopropylphenyl)methyl]-1,2-dihydro-3H-pyrazol-3-one.

$^1$H-NMR (CDCl$_3$) δ ppm: 1.07 (3H, t, J=7.3 Hz), 1.86 (3H, s), 2.01 (3H, s), 2.03 (3H, s) 2.06 (3H, s), 2.10 (3H, s), 2.10–2.25 (2H, m), 3.57 (1H, d, J=15.6 Hz), 3.63 (1H, d, J=15.6 Hz), 3.80–3.90 (1H, m), 4.05–4.20 (1H, m), 4.31 (1H, dd, J=4.0, 12.3 Hz), 5.15–5.35 (3H, m), 5.50–5.65 (1H, m), 6.10–6.25 (1H, m), 6.25–6.35 (1H, m), 6.95–7.10 (2H, m), 7.15–7.25 (2H, m)

REFERENCE EXAMPLE 7

1-Bromo-4-[(methoxymethyloxy)methyl]benzene

To a solution of 4-bromobenzyl alcohol (2.8 g) and diisopropylethylamine (2.5 g) in dichloromethane (30 mL) was added chloromethyl methyl ether (1.3 g) at 0° C., and the mixture was stirred at room temperature for 14 hours. To the reaction mixture was water, and the mixture was extracted diethyl ether. The organic layer was washed with water and dried over anhydrous magnesium sulfate, and the solvent was removed under reduced pressure. The residue was purified by column chromatography on silica gel (eluent: hexane/ethyl acetate=5/1) to give 1-bromo-4-[(methoxymethyloxy)methyl]benzene (3.0 g).

$^1$H-NMR (CDCl$_3$) δ ppm: 3.40 (3H, s), 4.54 (2H, s), 4.70 (2H, s), 7.20–7.30 (2H, m), 7.45–7.55 (2H, m)

REFERENCE EXAMPLE 8

4-(Thiazol-2-yl)benzyl alcohol

To a solution of 1-bromo-4-[(methoxymethyloxy)methyl]benzene (3.0 g) in tetrahydrofuran (52 mL) was added n-butyllithium (1.6 mol/L hexane solution, 9.3 mL) at −78° C., and the mixture was stirred for 30 minutes. To the reaction mixture was added triisopropyl borate (2.6 g), and the mixture was stirred at room temperature for 1 hour. To the reaction mixture was added 1 mol/L hydrochloric acid solution, and the mixture was extracted with ethyl acetate. The organic layer was washed with water and dried over anhydrous magnesium sulfate, and the solvent was removed under reduced pressure to give 4-[(methoxymethyloxy)methyl]phenylboric acid (2.5 g). A mixture of the obtained 4-[(methoxymethyloxy)methyl]phenylboric acid (2.5 g), 2-bromothiazole (1.2 g), cesium fluoride (2.2 g) and tetrakis(triphenylphosphine)palladium (0) (0.16 g) in 1,2-dimethoxyethane (40 mL), ethanol (10 mL) and water (10 mL) was stirred at 85° C. for 24 hours. The reaction mixture was concentrated under reduced pressure, and to the residue was added water, and the mixture was extracted with diethyl ether. The organic layer was washed with water and dried over anhydrous magnesium sulfate, and the solvent was removed under reduced pressure. The residue was purified by column chromatography on silica gel (eluent: hexane/ethyl acetate=5/1) to give 2-{4-[(methoxymethyloxy)methyl]phenyl}thiazole (0.80 g). To a solution of 2-{4-[(methoxymethyloxy)methyl]phenyl}thiazole (0.80 g) in ethanol (10 mL) was added 2 mol/L hydrochloric acid solution (5 mL), and the mixture was stirred at 50° C. for 5 hours. Concentrated hydrochloric acid (0.10 mL) was added to the mixture, and the mixture was stirred for 1 hour. To the reaction mixture was added water, and the mixture was extracted with ethyl acetate. The organic layer was dried over anhydrous magnesium sulfate, and the solvent was removed under reduced pressure. The residue was purified by column chromatography on silica gel (eluent: hexane/ethyl acetate=2/1-1/1) to give 4-(thiazol-2-yl)benzyl alcohol (0.33 g).

$^1$H-NMR (CDCl$_3$) δ ppm: 4.76 (2H, d, J=4.6 Hz), 7.33 (1H, d, J=3.7 Hz), 7.40–7.50 (2H, m), 7.87 (1H, d, J=3.7 Hz), 7.90–8.05 (2H, m)

EXAMPLE 7

5-Methyl-4-{[4-(thiazol-2-yl)phenyl]methyl}-1,2-dihdro-3H-pyrazol-3-one

The title compound was prepared in a similar manner to that described in Example 3 using 4-(thiazol-2-yl)benzyl alcohol instead of 4-cyclopropylbenzyl alcohol.

$^1$H-NMR (DMSO-d$_6$) δ ppm: 2.03 (3H, s), 3.60 (2H, s), 7.25–7.30 (2H, m), 7.74 (1H, d, J=3.1 Hz), 7.80–7.85 (2H, m), 7.88 (1H, d, J=3.1 Hz)

EXAMPLE 8

5-Methyl-3-(2,3,4,6-tetra-O-acetyl-β-D-glucopyranosyloxy)-4-{[4-(thiazol-2-yl)phenyl]methyl}-1H-pyrazole The title compound was prepared in a similar manner to that described in Example 4 using 5-methyl-4-{[4-(thiazol-2-yl)phenyl]methyl}-1,2-dihydro-3-pyrazol-3-one instead of 5-methyl-4-[(4-cyclopropylphenyl)methyl]-1,2-dihydro-3H-pyrazol-3-one.

$^1$H-NMR (CDCl$_3$) δ ppm: 1.88 (3H, s), 2.01 (3H, s), 2.03 (3H, s), 2.06 (3H, s), 2.13 (3H, s), 3.64 (1H, d, J=16.0 Hz), 3.71 (1H, d, J=16.0 Hz), 3.80–3.90 (1H, m), 4.14 (1H, dd, J=2.7, 12.2 Hz), 4.32 (1H, dd, J=3.8, 12.2 Hz), 5.15–5.35 (3H, m), 5.55–5.65 (1H, m), 7.15–7.25 (2H, m), 7.29 (1H, d, J=3.2 Hz), 7.80–7.90 (3H, m)

REFERENCE EXAMPLE 9

4-[3-(Benzyloxy)propyl]benzyl alcohol

To a solution of ethyl diethylphosphonoacetate (4.4 mL) in tetrahydrofuran (40 mL) was added sodium hydride (60%, 0.88 g) at 0° C., and the mixture was stirred for 10 minutes. To the reaction mixture was added a solution of terephthalaldehyde mono-(diethyl acetal) (4.2 g) in tetrahydrofuran (10 mL), and the mixture was stirred at room temperature for 1.5 hours. To the reaction mixture were added a saturated aqueous ammonium chloride solution and water, and the mixture was extracted with diethyl ether. The organic layer was washed with water and dried over anhydrous magnesium sulfate, and the solvent was removed under reduced pressure. The residue was purified by column chromatography on silica gel (eluent: hexane/ethyl acetate=3/1) to give ethyl 4-(diethoxymethyl)cinnamate (5.8 g). To a solution of the obtained ethyl 4-(diethoxymethyl)cinnamate (5.8 g) in tetrahydrofuran (50 mL) was added 5% platinum on carbon powder (0.58 g), and the mixture was stirred at room temperature under a hydrogen atmosphere for 10 hours. Insoluble materials was removed by filtration, and the filtrate was concentrated under reduced pressure. A solution of the residue in tetrahydrofuran (20 mL) was added to a suspension of lithium aluminum hydride (1.1 g) in tetrahydrofuran (100 mL) at 0° C. The reaction mixture was heated at 70° C. and stirred for 40 minutes. After the reaction mixture was cooled to 0° C., water (1.1 mL), 15% aqueous sodium hydroxide solution (1.1 mL) and water (3.3 mL) were added, and the mixture was stirred at room temperature for 10 minutes. Insoluble materials were removed by filtration, and the solvent of the filtrate was removed under reduced pressure to give 4-(3-hydroxypropyl)benzaldehyde diethyl acetal (4.7 g). To a solution of the obtained 4-(3-hydroxypropyl)benzaldehyde diethyl acetal (4.7 g) in dimethylformamide (100 mL) was added sodium hydride (60%, 1.2 g) at 0° C., and the mixture was stirred for 5 minutes. To the reaction mixture was added benzyl bromide (2.5 mL), and the mixture was stirred at room temperature for 72 hours. Water was added to the reaction mixture, and the mixture was extracted with hexane. The organic layer was washed with water and dried over anhydrous magnesium sulfate, and the solvent was removed under reduced pressure to give 4-[3-(benzyloxy)propyl]benzaldehyde diethyl acetal (6.4 g). To a solution of the obtained 4-[3-(benzyloxy)propyl]benzaldehyde diethyl acetal (6.4 g) in tetrahydrofuran (60 mL) was added 2 mol/L hydrochloric acid solution (10 mL) at 0° C., and the mixture was stirred for 1 hour. To the reaction mixture was added water, and the mixture was extracted with diethyl ether. The organic layer was washed with a saturated aqueous sodium hydrogen carbonate solution and dried over anhydrous magnesium sulfate, and the solvent was removed under reduced pressure. The residue was dissolved in ethanol (50 mL), and to the solution was added sodium borohydride (1.1 g) at 0° C. The mixture was stirred for 14 hours while gradually returning to room temperature. To the reaction mixture was added methanol, and the mixture was concentrated under reduced pressure. To the residue was added ethyl acetate, and the mixture was washed with water and dried over anhydrous magnesium sulfate. The solvent was removed under reduced pressure, and the residue was purified by column chromatography on silica gel (eluent: hexane/ethyl acetate=3/1-2/1) to give 4-[3-(benzyloxy)propyl]benzyl alcohol (3.7 g).

$^1$H-NMR (CDCl$_3$) δ ppm: 1.85–2.00 (2H, m), 2.65–2.80 (2H, m), 3.49 (2H, t, J=6.4 Hz), 4.51 (2H, s), 4.66 (2H, d, J=5.7 Hz), 7.15–7.40 (9H, m)

EXAMPLE 9

4-({4-[3-(Benzyloxy)propyl]phenyl}methyl)-5-trifluoromethyl-1,2-dihydro-3H-pyrazol-3-one To a solution of 4-[3-(benzyloxy)propyl]benzyl alcohol (2.0 g) in tetrahydrofuran (26 mL) were added triethylamine (1.1 mL) and methanesulfonyl chloride (0.60 mL) at 0° C., and the mixture was stirred at room temperature for 2 hours. Insoluble materials was removed by filtration. A solution of the obtained 4-[3-(benzyloxy)propyl]benzyl methanesulfonate in tetrahydrofuran was added to a suspension of sodium hydride (60%, 0.31 g) and ethyl 4,4,4-trifluoroacetoacetate (1.1 mL) in 1,2-dimethoxyethane (26 mL), and the mixture was stirred at 80° C. for 16 hours. To the reaction mixture was added a saturated aqueous ammonium chloride solution, and the mixture was extracted with diethyl ether. The extract was washed with water and dried over anhydrous magnesium sulfate. The solvent was removed under reduced pressure, and the residue was dissolved in toluene (20 mL). To the solution was added anhydrous hydrazine (0.74 mL), and the mixture was stirred at 80° C. for 18 hours. The reaction mixture was concentrated under reduced pressure, and the residue was purified by column chromatography on silica gel (eluent: dichloromethane/methanol=10/1) and successively by column chromatography on silica gel (eluent: dichloromethane/methanol=20/1) to give 4-({4-[3-(benzyloxy)propyl]phenyl}-methyl)-5-trifluoromethyl-1,2-dihydro-3H-pyrazol-3-one (0.84 g).

$^1$H-NMR (CDCl$_3$) δ ppm: 1.85–1.95 (2H, m), 2.60–2.70 (2H, m), 3.48 (2H, t, J=6.5 Hz), 3.79 (2H, s), 4.49 (2H, s), 7.05–7.20 (4H, m), 7.25–7.40 (5H, m)

EXAMPLE 10

4-({4-[3-(Benzyloxy)propyl]phenyl}methyl)-5-trifluoromethyl-3-(2,3,4,6-tetra-O-acetyl-β-D-glucopyranosyloxy)-1H-pyrazole To a solution of 4-({4-[3-(benzyloxy)propyl]phenyl}methyl)-5-trifluoromethyl-1,2-dihydro-3H-pyrazole-3-one (0.83 g) and acetobromo-α-D-glucose (1.5 g) in acetonitrile (12 mL) was added potassium carbonate (0.55 g), and the mixture was stirred at 60° C. for 20 hours. Insoluble materials were removed by filtration, and the solvent of the filtrate was removed under reduced pressure. The residue was purified by column chromatography on silica gel (eluent: hexane/ethyl acetate=1/1-1/2) to give 4-({4-[3-(benzyloxy)propyl]phenyl}methyl)-5-trifluoromethyl-3-(2,3,4,6-tetra-O-acetyl-β-D-glucopyranosyloxy)-1H-pyrazole (0.64 g).

$^1$H-NMR (CDCl$_3$) δ ppm: 1.80–1.95 (5H, m), 2.02 (3H, s), 2.04 (3H, s), 2.07 (3H, s), 2.60–2.70 (2H, m), 3.47 (2H, t, J=6.2 Hz), 3.74 (2H, s), 3.75–3.85 (1H, m), 4.18 (1H, dd, 2.2, 12.7 Hz), 4.26 (1H, dd, 4.5, 12.7 Hz), 4.50 (2H, s), 5.15–5.35 (3H, m), 5.35–5.45 (1H, m), 7.00–7.15 (4H, m), 7.20–7.40 (5H, m)

EXAMPLE 11

4-{[4-(3-Hydroxypropyl)phenyl]methyl}-5-trifluoromethyl-3-(2,3,4,6-tetra-O-acetyl-β-D-glucopyranosyloxy)-1H-pyrazole To a solution of 4-{[4-(3-benzyloxy)propyl]phenyl}methyl)-5-trifluoromethyl-3-(2,3,4,6-tetra-O-acetyl-β-D-glucopyranosyloxy)-1H-pyrazole (0.64 g) in methanol (10 mL) was added 10% palladium-carbon powder (0.13 g), and the mixture was stirred at room temperature under a hydrogen atmosphere for 11 hours. Insoluble materials were removed by filtration, the solvent of the filtrate was removed under reduced pressure. The residue was purified by column chromatography on silica gel (eluent: hexane/ethyl acetate=1/2) to give 4-{[4-(3-hydroxypropyl)phenyl]methyl}-5-trifluoromethyl-3-(2,3,4,6-tetra-O-acetyl-β-D-glucopyranosyloxy)-1H-pyrazole (0.45 g).

$^1$H-NMR (CDCl$_3$) δ ppm: 1.80–1.90 (2H, m), 1.92 (3H, s), 2.03 (3H, s), 2.04 (3H, s), 2.09 (3H, s), 2.60–2.70 (2H, m), 3.65 (2H, t, J=6.3 Hz), 3.75 (2H, s), 3.75–3.85 (1H, m), 4.15–4.30 (2H, m), 5.10–5.40 (4H, m), 7.05–7.15 (4H, m)

REFERENCE EXAMPLE 10

4-(2-Methylprop-1-en-1-yl)benzyl alcohol

To a suspension of isopropyltriphenylphosphonium iodide (9.5 g) in tetrahydrofuran (90 mL) was added n-butyllithium (1.5 mol/L hexane solution, 15 mL) at 0° C., and the mixture was stirred for 15 minutes. To the reaction mixture was added a solution of methyl terephthalaldehydate (3.3 g) in tetrahydrofuran (10 mL), and the mixture was stirred at room temperature for 3 hours. The reaction mixture was poured into a saturated aqueous ammonium chloride solution, and the mixture was extracted with diethyl ether. The organic layer was dried over anhydrous magnesium sulfate, and the solvent was removed under reduced pressure. The residue was purified by column chromatography on aminopropyl silica gel (eluent: hexane/ethyl acetate=3/1) and then by column chromatography on silica gel (eluent: dichloromethane/ethyl acetate=10/1) to give methyl 4-(2-methylprop-1-en-1-yl)benzoate (3.4 g). To a suspension of lithium aluminum hydride (0.68 g) in diethyl ether (120 mL) was added a solution of methyl 4-(2-methylprop-1-en-1-yl) benzoate (3.4 g) in diethyl ether (30 mL) at 0° C., and the mixture was heated under reflux for 50 minutes. After the reaction mixture was cooled to 0° C., water (0.69 mL), 15% aqueous sodium hydroxide solution (0.69 mL) and water (2 mL) were added, and the mixture was stirred at room temperature for 30 minutes. Insoluble materials were removed by filtrate, and the solvent of the filtrate was removed under reduced pressure. The residue was purified by column chromatography on silica gel (eluent: hexane/ ethyl acetate=4/1-2/1) to give 4-(2-methylprop-1-en-1-yl) benzyl alcohol (2.8 g).

$^1$H-NMR (CDCl$_3$) δ ppm: 1.60 (1H, t, J=5.6 Hz), 1.86 (3H, s), 1.90 (3H, s), 4.67 (2H, d, J=5.6 Hz), 6.26 (1H, s), 7.15–7.25 (2H, m), 7.25–7.35 (2H, m)

EXAMPLE 12

5-Methyl-4-{[4-(2-methylprop-1-en-1-yl)phenyl] methyl}-1,2-dihydro-3H-pyrazol-3-one To a solution of 4-(2-methylprop-1-en-1-yl)benzyl alcohol (0.60 g) and carbon tetrabromide (1.2 g) in dichloromethane (12 mL) was added triphenylphosphine (0.97 g) at 0° C., and the mixture was stirred at room temperature for 3.5 hours. To the reaction mixture was added water, and the mixture was extracted with hexane. The organic layer was washed with water and dried over anhydrous magnesium sulfate. The solvent was removed under reduced pressure, and the residue was purified by column chromatography on silica gel (eluent: hexane) to give 4-(2-methylprop-1-en-1-yl)benzyl bromide. To a solution of methyl acetoacetate (0.44 mL) in tetrahydrofuran (17 mL) was added sodium hydride (60%, 0.18 g) at 0° C., and the mixture was stirred for 10 minutes. To the reaction mixture was added a solution of 4-(2-methylprop-1-en-1-yl)benzyl bromide in tetrahydrofuran (3 mL), and the mixture was heated under reflux for 3.5 hours. A saturated aqueous ammonium chloride solution was added to the reaction mixture, and the mixture was extracted with diethyl ether. The organic layer was washed with water and dried over anhydrous magnesium sulfate. The solvent was removed under reduced pressure, and the residue was dissolved in toluene (8 mL). To the solution was added hydrazine monohydrate (0.54 mL), and the mixture was stirred at 80° C. for 30 minutes. The reaction mixture was cooled to 0° C., and the resulting precipitates were collected by filtration, washed with water and hexane, and dried under reduced pressure to give 5-methyl-4-{[4-(2-methylprop-1-en-1-yl)phenyl]methyl}-1,2-dihydro-3H-pyrazol-3-pyrazol-3-one (0.31 g).

$^1$H-NMR (DMSO-d$_6$) δ ppm: 1.79 (3H, d, J=0.8 Hz), 1.85 (3H, d, J=1.3 Hz), 2.01 (3H, s), 3.52 (2H, s), 6.15–6.25 (1H, m), 7.05–7.15 (4H, m)

EXAMPLE 13

5-Methyl-4-{[4-(2-methylprop-1-en-1-yl)phenyl] methyl}-3-(2,3,4,6-tetra-O-acetyl-β-D-glucopyranosyloxy)-1H-pyrazole The title compound was prepared in a similar manner to that described in Example 4 using 5-methyl-4-{[4-(2-methylprop-1-en-1-yl)phenyl]methyl}-1,2-dihydro-3H-pyrazol-3-one instead of 5-methyl-4-[(4-cyclopropylphenyl)methyl]-1,2-dihydro-3H-pyrazol-3-one.

$^1$H-NMR (CDCl$_3$) δ ppm: 1.83 (3H, s), 1.86 (3H, s), 1.87 (3H, s), 2.01 (3H, s), 2.03 (3H, s), 2.06 (3H, s), 2.12 (3H, s), 3.57 (1H, d, J=15.6 Hz), 3.65 (1H, d, J=15.6 Hz), 3.80–3.90 (1H, m), 4.13 (1H, dd, J=2.1, 12.6 Hz), 4.31 (1H, dd, J=3.9, 12.6 Hz), 5.15–5.35 (3H, m), 5.50–5.65 (1H, m), 6.15–6.25 (1H, m), 7.00–7.15 (4H, m)

REFERENCE EXAMPLE 11

4-[(4-Bromophenyl)methyl]-5-methyl-1,2-dihdro-3H-pyrazol-3-one

To a solution of methyl acetoacetate (3.2 mL) in tetrahydrofuran (100 mL) was added sodium hydride (60%, 1.3 g) at 0° C., and the mixture was stirred for 5 minutes. To the reaction mixture was added 4-bromobenzyl bromide (7.5 g), and the mixture was heated under reflux for 3 hours. To the reaction mixture was added water, and the mixture was extracted with diethyl ether. The organic layer was washed with water and dried over anhydrous magnesium sulfate. The solvent was removed under reduced pressure, and the residue was dissolved in toluene (50 mL). To the solution was added hydrazine monohydrate (4.4 mL), and the mixture was stirred at 80° C. for 30 minutes. The reaction mixture was cooled to room temperature, and the resulting precipitates were collected by filtration, washed with water and hexane, and dried under reduced pressure to give 4-[(4-bromophenyl)methyl]-5-methyl-1,2-dihdro-3H-pyrazol-3-one (4.0 g).

$^1$H-NMR (DMSO-d$_6$) δ ppm: 2.00 (3H, s), 3.52 (2H, s), 7.05–7.15 (2H, m), 7.35–7.45 (2H, m)

REFERENCE EXAMPLE 12

4-[(4-Bromophenyl)methyl]-5-methyl-3-(2,3,4,6-tetra-O-acetyl-β-D-glucopyranosyloxy)-1H-pyrazole The title compound was prepared in a similar manner to that described in Example 4 using 4-[(4-bromophenyl)methyl]-5-methyl-1,2-dihydro-3H-pyrazol-3-one instead of 5-methyl-4-[(4-cyclopropylphenyl)methyl]-1,2-dihydro-3H-pyrazol-3-one.

$^1$H-NMR (CDCl$_3$) δ ppm: 1.89 (3H, s), 2.01 (3H, s), 2.03 (3H, s), 2.07 (3H, s), 2.12 (3H, s), 3.54 (1H, d, J=16.0 Hz), 3.60 (1H, d, J=16.0 Hz), 3.80–3.90 (1H, m), 4.05–4.20 (1H, m), 4.31 (1H, dd, J=3.3, 12.3 Hz), 5.10–5.35 (3H, m), 5.55–5.65 (1H, m), 6.95–7.10 (2H, m), 7.30–7.40 (2H, m)

EXAMPLE 14

4-{[4-(4-Fluorophenyl)phenyl]methyl}-5-methyl-3-(2,3,4,6-tetra-O-acetyl-β-acetyl-β-D-glucopyranosyloxy)-1H-pyrazole A mixture of 4-[(4-bromophenyl)methyl]-5-methyl-3-(2,3,4,6-tetra-O-acetyl-β-D-glucopyranosyloxy)-1H-pyrazole (0.099 g), 4-fluorophenylboronic acid (0.046 g), cesium fluoride (0.050 g) and tetrakis(triphenylphosphine)palladium(0) (0.0038 g) in 1,2-dimethoxyethane (1.3 mL), ethanol (0.3 mL) and water (0.3 mL) was stirred at 85° C. for 18 hours. The reaction mixture was purified by column chromatography on silica gel (eluent: hexane/ethylacetate=1/1-1/2-1/5) to give 4-{[4-(4-fluorophenyl)phenyl]methyl}-5-methyl-3-(2,3,4,6-tetra-O-acetyl-β-D-glucopyranosyloxy)-1H-pyrazole (0.061 g).

$^1$H-NMR (CDCl$_3$) δ ppm: 1.86 (3H, s), 2.01 (3H, s), 2.03 (3H, s), 2.05 (3H, s), 2.16 (3H, s), 3.64 (1H, d, J=15.9 Hz), 3.70 (1H, d, J=15.9 Hz), 3.80–3.90 (1H, m), 4.14 (1H, dd, J=2.0, 12.5 Hz), 4.31 (1H, dd, J=4.1, 12.5 Hz), 5.15–5.30 (3H, m), 5.55–5.65 (1H, m), 7.05–7.15 (2H, m), 7.15–7.25 (2H, m), 7.35–7.55 (4H, m)

REFERENCE EXAMPLE 13

4-Cyclobutyloxybenzyl alcohol

To a suspension of 4-hydroxybenzaldehyde (0.12 g) and cesium carbonate (0.49 g) in N,N-dimethylformamide (2 mL) was added cyclobutyl bromide (0.15 g), and the mixture was stirred at 65° C. overnight. To the reaction mixture was added 1 mol/L aqueous sodium hydroxide solution, and the mixture was extracted with diethyl ether. The organic layer was washed with 0.5 mol/L aqueous sodium hydroxide solution, water and brine, and dried over anhydrous magnesium sulfate. The solvent was removed under reduced pressure to give 4-cyclobutyloxybenzaldehyde (0.13 g). To a solution of the obtained 4-cyclobutyloxybenzaldehyde (0.13 g) in methanol (10 mL) was added sodium borohydride (0.056 g), and the mixture was stirred at room temperature overnight. To the reaction mixture was added 1 mol/L hydrochloric acid solution, and the mixture was extracted with diethyl ether. The organic layer was dried over anhydrous magnesium sulfate, and the solvent was removed under reduced pressure to give 4-cyclobutyloxybenzyl alcohol (0.12 g).

$^1$H-NMR (CDCl$_3$) δ ppm: 1.50 (1H, t, J=5.8 Hz), 1.60–1.75 (1H, m), 1.80–1.95 (1H, m), 2.10–2.25 (2H, m), 2.40–2.50 (2H, m), 4.61 (2H, d, J=5.8 Hz), 4.60–4.70 (1H, m), 6.75–6.85 (2H, m), 7.20–7.30 (2H, m)

EXAMPLE 15

4-{[4-(Cyclobutyloxy)phenyl]methyl}-5-methyl-1,2-dihdro-3H-pyrazol-3-one

The title compound was prepared in a similar manner to that described in Example 3 using 4-cyclobutyloxybenzyl alcohol instead of 4-cyclopropylbenzyl alcohol.

$^1$H-NMR (DMSO-d$_6$) δ ppm: 1.55–1.70 (1H, m), 1.70–1.85 (1H, m), 1.90–2.05 (5H, m), 2.30–2.45 (2H, m), 3.50 (2H, s), 4.55–4.65 (1H, m), 6.65–6.75 (2H, m), 6.95–7.10 (2H, m)

EXAMPLE 16

4-{[4-(Cyclobutyloxy)phenyl]methyl}-5-methyl-3-(2,3,4,6-tetra-O-acetyl-β-D-glucopyranosyloxy)-1H-pyrazole The title compound was prepared in a similar manner to that described in Example 4 using 4-{[4-(cyclobutyloxy)phenyl]methyl}-5-methyl-1,2-dihydro-3H-pyrazol-3-one instead of 5-methyl-4-[(4-cyclopropylphenyl)methyl]-1,2-dihydro-3H-pyrazol-3-one.

$^1$H-NMR (CDCl$_3$) δ ppm: 1.55–1.95 (2H, m), 1.88 (3H, s), 2.01 (3H, s), 2.03 (3H, s), 2.05 (3H, s), 2.10 (3H, s), 2.00–2.25 (2H, m), 2.35–2.50 (2H, m), 3.52 (1H, d, J=15.6 Hz), 3.58 (1H, d, J=15.6 Hz), 3.80–3.90 (1H, m), 4.12 (1H, dd, J=2.4, 12.3 Hz), 4.30 (1H, dd, J=3.7, 12.3 Hz), 4.50–4.65 (1H, m), 5.15–5.35 (3H, m), 5.50–5.60 (1H, m), 6.65–6.75 (2H, m), 6.95–7.05 (2H, m)

REFERENCE EXAMPLE 14

4-({4-[4-(Benzyloxy)phenyl]phenyl}methyl)-5-methyl-3-(2,3,4,6-tetra-O-acetyl-β-D-glucopyranosyloxy)-1H-pyrazole The title compound was prepared in a similar manner to that described in Example 14 using 4-(benzyloxy)phenylboronic acid instead of 4-fluorophenylboronic acid.

$^1$H-NMR (CDCl$_3$) δ ppm: 1.85 (3H, s), 2.01 (3H, s), 2.03 (3H, s), 2.06 (3H, s), 2.15 (3H, s), 3.62 (1H, d, J=16.0 Hz), 3.69 (1H, d, J=16.0 Hz), 3.80–3.90 (1H, m), 4.10–4.20 (1H, m), 4.25–4.40 (1H, m), 5.10 (2H, s), 5.15–5.35 (3H, m), 5.55–5.65 (1H, m), 6.95–7.55 (13H, m)

EXAMPLE 17

4-{[4-(4-Hydroxyphenyl)phenyl]methyl}-5-methyl-3-(2,3,4,6-tetra-O-acetyl-β-D-glucopyranosyloxy)-1H-pyrazole To a solution of 4-({4-[4-(benzyloxy)phenyl]phenyl}methyl)-5-methyl-3-(2,3,4,6-tetra-O-acetyl-β-D-glucopyranosyloxy)-1H-pyrazole (0.14 g) in methanol (3 mL) was added 10% palladium-carbon powder (0.030 g), and the mixture was stirred at room temperature under a hydrogen atmosphere for 11 hours. Insoluble materials were removed by filtration, and the solvent of the filtrate was removed under reduced pressure. The residue was purified by column chromatography on aminopropyl silica gel (eluent: hexane/ethyl acetate=1/1-1/5-dichloromethane/methanol=10/1) to give 4-{[4-(4-hydroxyphenyl)phenyl]methyl}-5-methyl-3-(2,3,4,6-tetra-O-acetyl-β-D-glucopyranosyloxy)-1H-pyrazole (0.071 g).

$^1$H-NMR (CDCl$_3$) δ ppm: 1.85 (3H, s), 2.01 (3H, s), 2.03 (3H, s), 2.05 (3H, s), 2.15 (3H, s), 3.62 (1H, d, J=15.7 Hz), 3.69 (1H, d, J=15.7 Hz), 3.80–3.90 (1H, m), 4.10–4.20 (1H, m), 4.31 (1H, dd, J=3.9, 12.6 Hz), 5.12 (1H, brs), 5.15–5.35 (3H, m), 5.55–5.65 (1H, m), 6.80–6.90 (2H, m), 7.10–7.25 (2H, m), 7.35–7.50 (4H, m)

EXAMPLE 18

4-{[4-(3-Fluorophenyl)phenyl]methyl}-5-methyl-3-(2,3,4,6-tetra-O-acetyl-β-D-glucopyranosyloxy)-1H-pyrazole The title compound was prepared in a similar manner to that described in Example 14 using 3-fluorophenylboronic acid instead of 4-fluorophenylboronic acid.

$^1$H-NMR (CDCl$_3$) δ ppm: 1.86 (3H, s), 2.01 (3H, s), 2.03 (3H, s), 2.06 (3H, s), 2.16 (3H, s), 3.63 (1H, d, J=16.1 Hz), 3.71 (1H, d, J=16.1 Hz), 3.80–3.90 (1H, m), 4.05–4.20 (1H, m), 4.32 (1H, dd, J=4.0, 12.4 Hz), 5.15–5.35 (3H, m), 5.55–5.65 (1H, m), 6.95–7.05 (1H, m), 7.15–7.50 (7H, m)

REFERENCE EXAMPLE 15

4-(Pyridin-2-yl)benzyl chloride

To a solution of 2-(p-tolyl)pyridine (1.7 g) and N-chlorosuccinimide (1.5 g) in carbon tetrachloride (30 mL) was added α,α-azobisisobutyronitrile (0.033 g), and the mixture was heated under reflux for 5 hours. Insoluble materials were removed by filtration, and the filtrate was concentrated under reduced pressure. The residue was purified by column chromatography on silica gel (eluent: hexane/ethyl acetate=5/1-3/1) to give 4-(pyridin-2-yl)benzyl chloride (1.1 g).

$^1$H-NMR (CDCl$_3$) δ ppm: 4.65 (2H, s), 7.20–7.30 (1H, m), 7.45–7.55 (2H, m), (2H, m), 7.95–8.05 (2H, m), 8.65–8.75 (1H, m)

EXAMPLE 19

5-Methyl-4-{[4-(pyridin-2-yl)phenyl]methyl}-1,2-dihydro-3H-pyrazol-3-one

The title compound was prepared in a similar manner to that described in Reference Example 11 using 4-(pyridin-2-yl)benzyl chloride instead of 4-bromobenzyl bromide.

$^1$H-NMR (DMSO-d$_6$) δ ppm: 2.03 (3H, s), 3.60 (2H, s), 7.20–7.30 (2H, m), 7.31 (1H, ddd, J=1.2, 4.7, 7.3 Hz), 7.80–8.00 (4H, m), 8.63 (1H, ddd, J=0.9, 1.6, 4.7 Hz)

EXAMPLE 20

3-(β-D-Glucopyranosyloxy)-5-methyl-4-{[4-(cyclopropylidenemethyl)phenyl]methyl}-1H-pyrazole A solution of 5-methyl-4-{[4-(cyclopropylidenemethyl)phenyl]methyl}-3-(2,3,4,6-tetra-O-acetyl-β-D-glucopyranosyloxy)-1H-pyrazole (0.010 g) in methanol (2 mL) was added sodium methoxide (28% methanol solution, 0.0020 mL), and the mixture was stirred at room temperature for 30 minutes. The reaction mixture was concentrated under reduced pressure, and the residue was purified by solid phase extraction on ODS (washing solvent: distilled water, eluent: methanol) to give 3-(β-D-glucopyranosyloxy)-5-methyl-4-{[4-(cyclopropylidenemethyl)phenyl]methyl}-1H-pyrazole (0.0070 g).

$^1$H-NMR (CD$_3$OD) δ ppm: 1.05–1.20 (2H, m), 1.30–1.45 (2H, m), 2.06 (3H, s), 3.25–3.45 (4H, m), 3.60–3.90 (4H, m), 5.00–5.10 (1H, m), 6.60–6.70 (1H, m), 7.00–7.20 (2H, m), 7.30–7.45 (2H, m)

EXAMPLE 21

3-(β-D-Glucopyranosyloxy)-5-methyl-4-[(4-cyclopropylphenyl)methyl]-1H-pyrazole

To a solution of 5-methyl-4-[(4-cyclopropylphenyl)methyl]-3-(2,3,4,6-tetra-O-acetyl-β-D-glucopyranosyloxy)-1H-pyrazole (0.14 g) in ethanol (8.4 mL) was added 2 mol/L aqueous sodium hydroxide solution (0.63 mL), and the mixture was stirred at room temperature for 30 minutes. The solvent was removed under reduced pressure, and the residue was purified by column chromatography on silica gel (eluent: dichloromethane/methanol=6/1) to give 3-(β-D-glucopyranosyloxy)-5-methyl-4-[(4-cyclopropylphenyl)methyl]-1H-pyrazole (0.087 g).

$^1$H-NMR (CD$_3$OD) δ ppm: 0.55–0.70 (2H, m), 0.85–0.95 (2H, m), 1.75–1.90 (1H, m), 2.04 (3H, s), 3.25–3.45 (4H, m), 3.60–3.90 (4H, m), 5.00–5.10 (1H, m), 6.85–7.15 (4H, m)

EXAMPLE 22

(E)-4-{[4-(But-1-en-1-yl)phenyl]methyl}-3-(β-D-glucopyranosyloxy)-5-methyl-1H-pyrazole The title compound was prepared in a similar manner to that described in Example 21 using (E)-4-{[4-(but-1-en-1-yl)phenyl]methyl}-5-methyl-3-(2,3,4,6-tetra-O-acetyl-β-D-glucopyranosyloxy)-1H-pyrazole instead of 5-methyl-4-[(4-cyclopropylphenyl)methyl]-3-(2,3,4,6-tetra-O-acetyl-β-D-glucopyranosyloxy)-1H-pyrazole.

$^1$H-NMR (CD$_3$OD) δ ppm: 1.07 (3H, t, J=7.4 Hz), 2.05 (3H, s), 2.15–2.25 (2H, m), 3.30–3.45 (4H, m), 3.60–3.80 (3H, m), 3.80–3.90 (1H, m), 5.00–5.10 (1H, m), 6.22 (1H, dt, J=16.0, 6.5 Hz), 6.33 (1H, d, J=16.0 Hz), 7.05–7.15 (2H, m), 7.20–7.25 (2H, m)

EXAMPLE 23

3-(β-D-Glucopyranosyloxy)-5-methyl-4-{[4-(thiazol-2-yl)phenyl]methyl}-1H-pyrazole The title compound was prepared in a similar manner to that described in Example 21 using 5-methyl-3-(2,3,4,6-tetra-O-acetyl-β-D-glucopyranosyloxy)-4-{[4-(thiazol-2-yl)phenal]methyl}-1H-pyrazole instead of 5-methyl-4-[(4-cyclopropylphenyl)methyl]-3-(2,3,4,6-tetra-O-acetyl-β-D-glucopyranosyloxy)-1H-pyrazole.

$^1$H-NMR (CD$_3$OD) δ ppm: 2.10 (3H, s), 3.25–3.50 (4H, m), 3.60–3.90 (4H, m), 5.05–5.15 (1H, m), 7.30–7.40 (2H, m), 7.55 (1H, d, J=3.1 Hz), 7.80–7.90 (3H, m)

EXAMPLE 24

3-(β-D-Glucopyranosyloxy)-4-{[4-(3-hydroxypropyl)phenyl]methyl}-5-trifluoromethyl-1H-pyrazole To a solution of 4-{[4-(3-hydroxypropyl)phenyl]methyl}-5-trifluoromethyl-3-(2,3,4,6-tetra-O-acetyl-β-D-glucopyranosyloxy)-1H-pyrazole (0.45 g) in methanol (7 mL) was added sodium methoxide (28% methanol solution, 0.068 mL), and the mixture was stirred at room temperature for 30 minutes. The reaction mixture was concentrated under reduced pressure, and the residue was purified by column chromatography on silica gel (eluent: dichloromethane/methanol=6/1) to give 3-(β-D-glucopyranosyloxy)-4-{[4-(3-hydroxypropyl)phenyl]methyl}-trifluoromethyl-1H-pyrazole (0.17 g).

¹H-NMR (CD₃OD) δ ppm: 1.75–1.85 (2H, m), 2.62 (2H, t, J=7.6 Hz), 3.30–3.45 (4H, m), 3.54 (2H, t, J=6.2 Hz), 3.68 (1H, dd, J=5.2, 12.2 Hz), 3,75–3.95 (3H, m), 4.95–5.05 (1H, m), 7.05–7.15 (4H, m)

EXAMPLE 25

3-(β-D-Glucopyranosyloxy)-5-methyl-4-{[4-(2-methylprop-1-en-1-yl)phenyl]methyl}-1H-pyrazole The title compound was prepared in a similar manner to that described in Example 21 using 5-methyl-4-{[4-(2-methylprop-1-en-1-yl)phenyl]methyl}-3-(2,3,4,6-tetra-O-acetyl-β-D-glucopyranosyloxy)-1H-pyrazole instead of 5-methyl-4-[(4-cyclopropylphenyl)methyl]-3-(2,3,4,6-tetra-O-acetyl-β-D-glucopyranosyloxy)-1H-pyrazole.

¹H-NMR (CDCl₃) δ ppm: 1.81 (3H, d, J=1.0 Hz), 1.86 (3H, s), 2.06 (3H, s), 3.25–3.45 (4H, m), 3.60–3.80 (3H, m), 3.80–3.90 (1H, m), 5.00–5.10 (1H, m), 6.15–6.25 (1H, m), 7.00–7.20 (4H, m)

EXAMPLE 26

4-{[4-(4-Fluorophenyl)phenyl]methyl}-3-(β-D-glucopyranosyloxy)-5-methyl-1H-pyrazole The title compound was prepared in a similar manner to that described in Example 21 using 4-{[4-(4-fluorophenyl)phenyl]methyl}-5-methyl-3-(2,3,4,6-tetra-O-acetyl-β-D-glucopyranosyloxy)-1H-pyrazole instead of 5-methyl-4-[(4-cyclopropylphenyl)methyl]-3-(2,3,4,6-tetra-O-acetyl-β-D-glucopyranosyloxy)-1H-pyrazole.

¹H-NMR (CD₃OD) δ ppm: 2.10 (3H, s), 3.30–3.45 (4H, m), 3.60–3.90 (4H, m), 5.05–5.15 (1H, m), 7.05–7.20 (2H, m), 7.25–7.35 (2H, m), 7.40–7.50 (2H, m), 7.50–7.65 (2H, m)

EXAMPLE 27

4-{[4-(Cyclobutyloxy)phenyl]methyl}-3-(β-D-glucopyranosyloxy)-5-methyl-1H-pyrazole The title compound was prepared in a similar manner to that described in Example 21 using 4-{[4-(cyclobutyloxy)phenyl]methyl}-5-methyl-3-(2,3,4,6-tetra-O-acetyl-β-D-glucopyranosyloxy)-1H-pyrazole instead of 5-methyl-4-[(4-cyclopropylphenyl)methyl]-3-(2,3,4,6-tetra-O-acetyl-β-D-glucopyranosyloxy)-1H-pyrazole.

¹H-NMR (CD₃OD) δ ppm: 1.60–1.90 (2H, m), 2.00–2.15 (5H, m), 2.35–2.50 (2H, m), 3.30–3.45 (4H, m), 3.60–3.75 (3H, m), 3.75–3.90 (1H, m), 4.50–4.70 (1H, m), 5.00–5.10 (1H, m), 6.65–6.75 (2H, m), 7.00–7.15 (2H, m)

EXAMPLE 28

3-(β-D-Glucopyranosyloxy)-5-methyl-1-isopropyl-4-[(4-cyclopropylphenyl)methyl]-1H-pyrazole To a suspension of 3-(β-D-glucopyranosyloxy)-5-methyl-4-[(4-cyclopropylphenyl)methyl]-1H-pyrazole (56 mg) and cesium carbonate (23 mg) in N,N-dimethylformamide (1.5 mL) was added 2-iodopropane (0.043 mL) at 80° C., and the mixture was stirred for 35 minutes. To the reaction mixture was added water, and the mixture was purified by solid phase extraction on ODS (washing solvent: distilled water, eluent: methanol). The obtained crude product was purified by preparative thin layer chromatography on silica gel (developing solvent: dichloromethane/methanol=7/1) to give 3-(β-D-glucopyranosyloxy)-5-methyl-1-isopropyl-4-[(4-cyclopropylphenyl)methyl]-1H-pyrazole )45 mg).

¹H-NMR (CD₃OD) δ ppm: 0.50–0.65 (2H, m), 0.80–0.95 (2H, m), 1.36 (3H, d, J=6.6 Hz), 1.37 (3H, d, J=6.6 Hz), 1.75–1.90 (1H, m), 2.07 (3H, s), 3.15–3.50 (4H, m), 3.60–3.85 (4H, m), 4.30–4.50 (1H, m), 4.95–5.10 (1H, m), 6.85–7.10 (4H, m)

EXAMPLE 29

3-(β-D-Glucopyranosyloxy)-4-{[4-(4-hydroxyphenyl)phenyl]methyl}-5-methyl-1H-pyrazole The title compound was prepared in a similar manner to that described in Example 21 using 4-{[4-(4-hydroxyphenyl)phenyl]methyl}-5-methyl-3-(2,3,4,6-tetra-O-acetyl-β-D-glucopyranosyloxy)-1H-pyrazole instead of 5-methyl-4-[(4-cyclopropylphenyl)methyl]-3-(2,3,4,6-tetra-O-acetyl-β-D-glucopyranosyloxy)-1H-pyrazole.

¹H-NMR (CD₃OD) δ ppm: 2.09 (3H, s), 3.25–3.45 (4H, m), 3.60–3.90 (4H, m), 5.00–5.10 (1H, m), 6.75–6.85 (2H, m), 7.15–7.25 (2H, m), 7.30–7.45 (4H, m)

EXAMPLE 30

4-{[4-(3-Fluorophenyl)phenyl]methyl}-3-(β-D-Glucopyranosyloxy)-5-methyl-1H-pyrazole The title compound was prepared in a similar manner to that described in Example 21 using 4-{[4-(3-fluorophenyl)phenyl]methyl}-5-methyl-3-(2,3,4,6-tetra-O-acetyl-β-D-glucopyranosyloxy)-1H-pyrazole instead of 5-methyl-4-[(4-cyclopropylphenyl)methyl]-3-(2,3,4,6-tetra-O-acetyl-β-D-glucopyranosyloxy)-1H-pyrazole.

¹H-NMR (CD₃OD) δ ppm: 2.10 (3H, s), 3.25–3.55 (4H, m), 3.60–3.90 (4H, m), 5.00–5.15 (1H, m), 6.95–7.10 (1H, m), 7.25–7.35 (3H, m), 7.35–7.45 (2H, m), 7.45–7.55 (2H, m)

EXAMPLE 31

3-(β-D-Glucopyranosyloxy)-5-methyl-4-{[4-(pyridin-2-yl)phenyl]methyl}-1H-pyrazole 5-Methyl-4-{[4-(pyridin-2-yl)phenyl]methyl}-3-(2,3,4,6-tetraacetyl-β-D-glucopyranosyloxy)-1H-pyrazole was prepared in a similar manner to that described in Example 4 using 5-methyl-4-{[4-(pyridin-2-yl)phenyl]methyl}-1,2-dihydro-3H-pyrazol-3-one instead of 5-methyl-4-[(4-cyclopropylphenyl)methyl]-1,2-dihydro-3H-pyrazol-3-one. Then the title compound was prepared in a similar manner to that described in Example 21 using 5-methyl-4-{[4-(pyridin-2-yl)phenyl]methyl}-3-(2,3,4,6-tetraacetyl-β-D-glucopyranosyloxy)-1H-pyrazole instead of 5-methyl-4-[(4-cyclopropylphenyl)methyl]-3-(2,3,4,6-tetra-O-acetyl-β-D-glucopyranosyloxy)-1H-pyrazole.

¹H-NMR (CD₃OD) δ ppm: 2.10 (3H, s), 3.30–3.45 (4H, m), 3.60–3.90 (4H, m), 5.00–5.15 (1H, m), 7.25–7.40 (3H, m), 7.75–7.95 (4H, m), 8.50–8.60 (1H, m)

EXAMPLE 32

3-(β-D-Glucopyranosyloxy)-5-methyl-1-(cyclopropylmethyl)-4-[(4-cyclopropylphenyl)methyl]-1H-pyrazole The title compound was prepared in a similar manner to that described in Example 28 using (bromomethyl)cyclopropane instead of 2-iodopropane.

$^1$H-NMR (CD$_3$OD) δ ppm: 0.25–0.40 (2H, m), 0.45–0.65 (4H, m), 0.80–0.95 (2H, m), 1.05–1.25 (1H, m), 1.75–1.90 (1H, m), 2.08 (3H, s), 3.25–3.45 (4H, m), 3.55–3.90 (6H, m), 5.00–5.10 (1H, m), 6.85–7.10 (4H, m)

EXAMPLE 33

3-(β-D-Glucopyranosyloxy)-1-(2-hydroxyethyl)-5-methyl-4-[(4-cyclopropylphenyl)methyl]-1H-pyrazole To a suspension of 3-(β-D-glucopyranosyloxy)-5-methyl-4-[(4-cyclopropylphenyl)methyl]-1H-pyrazole (33 mg) and cesium carbonate (138 mg) in N,N-dimethylformamide (1 mL) was added 2-bromoethyl acetate (0.035 mL) at 40° C., and the mixture was stirred for 2 hours. To the reaction mixture was added water, and the mixture was purified by solid phase extraction on ODS (washing solvent: distilled water, eluent: methanol). The obtained crude product was dissolved in methanol (1 mL), and to the solution was added 2 mol/L aqueous sodium hydroxide solution (0.04 mL), and the mixture was stirred at room temperature for 30 minutes. The solvent was removed under reduced pressure, and the residue was purified by column chromatography on ODS (developing solvent: methanol/water=3/2) to give 3-(β-D-glucopyranosyloxy)-1-(2-hydroxyethyl)-5-methyl-4-[(4-cyclopropylphenyl)methyl]-1H-pyrazole (8 mg).

$^1$H-NMR (CD$_3$OD) δ ppm: 0.45–0.55 (2H, m), 0.70–0.85 (2H, m), 1.65–1.80 (1H, m) 2.01 (3H, s), 3.15–3.35 (4H, m), 3.50–3.65 (3H, m), 3.65–3.75 (3H, m), 3.90 (2H, t, J=5.5 Hz), 4.95–5.05 (1H, m), 6.80–6.90 (2H, m), 6.90–7.00 (2H, m)

EXAMPLE 34

3-(β-D-Glucopyranosyloxy)-5-methyl-1-cyclopentyl-4-[(4-cyclopropylphenyl)methyl]-1H-pyrazole The title compound was prepared in a similar manner to that described in Example 28 using bromocyclopentane instead of 2-iodopropane.

$^1$H-NMR (CD$_3$OD) δ ppm: 0.55–0.65 (2H, m), 0.80–1.00 (2H, m), 1.50–1.75 (2H, m), 1.75–2.10 (7H, m), 2.07 (3H, s), 3.15–3.45 (4H, m), 3.55–3.85 (4H, m), 4.45–4.65 (1H, m), 5.00–5.10 (1H, m), 6.85–7.10 (4H, m)

REFERENCE EXAMPLE 16

4-[(4-Ethylphenyl)methyl]-5-methyl-1,2-dihdro-3H-pyrazol-3-one

To a solution of 4-ethylbenzyl alcohol (2.5 g) and triethylamine (2.5 mL) in tetrahydrofuran (35 mL) was added methanesulfonyl chloride (1.4 mL), and the mixture was stirred at room temperature for 1 hour. Insoluble materials were removed by filtration. A solution of the obtained 4-ethylbenzyl methanesulfonate in tetrahydrofuran was added to a suspension of sodium hydride (60%, 0.72 g) and methyl acetoacetate (1.9 mL) in 1,2-dimethoxyethane (40 mL), and the mixture was stirred at 70° C. for 2 hours. To the reaction mixture was added a saturated aqueous ammonium chloride solution, and the mixture was extracted with diethyl ether. The organic layer was dried over anhydrous magnesium sulfate, and the solvent was removed under reduced pressure. To a solution of the residue in toluene (50 mL) was added hydrazine monohydrate (2.7 mL), and the mixture was stirred at 80° C. for 2 hours. After the reaction mixture was cooled to room temperature, hexane was added to the mixture. The precipitates were collected by filtration, washed with water and hexane, and dried under reduced pressure to give 4-[(4-ethylphenyl)methyl]-5-methyl-1,2-dihdro-3H-pyrazol-3-one (1.2 g).

$^1$H-NMR (DMSO-d$_6$) δ ppm: 1.13 (3H, t, J=7.6 Hz), 2.00 (3H, s), 2.45–2.60 (2H, m), 3.49 (2H, s), 7.00–7.15 (4H, m)

REFERENCE EXAMPLE 17

4-[(4-Ethylphenyl)methyl]-5-methyl-3-(2,3,4,6-tetra-O-acetyl-β-D-glucopyranosyloxy)-1H-pyrazole To a suspension of 4-[(4-ethylphenyl)methyl]-5-methyl-1,2-dihdro-3H-pyrazol-3-one (0.65 g) and acetobromo-α-D-glucose (1.2 g) in tetrahydrofuran (15 mL) was added silver carbonate (0.83 g), and the mixture was stirred at 60° C. overnight under light shielding. The reaction mixture was purified by column chromatography on aminopropyl silica gel (eluent: tetrahydrofuran), and successively by column chromatography on silica gel (eluent: hexane/ethyl acetate=1/3) to give 4-[(4-ethylphenyl)methyl]-5-methyl-3-(2,3,4,6-tetra-O-acetyl-β-D-glucopyranosyloxy)-1H-pyrazole (0.61 g.

$^1$H-NMR (CDCl$_3$) δ ppm: 1.19 (3H, t, J=7.6 Hz), 1.86 (3H, s), 2.02 (3H, s), 2.03 (3H, s), 2.07 (3H, s), 2.12 (3H, s), 2.58 (2H, q, J=7.6 Hz), 3.56 (1H, d, J=15.7 Hz), 3.63 (1H, d, J=15.7 Hz), 3.80–3.90 (1H, m), 4.13 (1H, dd, J=2.4, 12.5 Hz), 4.31 (1H, dd, J=4.1, 12.5 Hz), 5.10–5.35 (3H, m), 5.50–5.65 (1H, m), 7.00–7.15 (4H, m), 8.91 (1H, brs)

REFERENCE EXAMPLE 18

1-(2-Benzyloxyethyl)-4-[(4-ethylphenyl)methyl]-3-(β-D-glucopyranosyloxy)-5-methyl-1H-pyrazole To a suspension of 4-[(4-ethylphenyl)methyl]-5-methyl-3-(2,3,4,6-tetra-O-acetyl-β-D-glucopyranosyloxy)-1H-pyrazole (0.030 g) and cesium carbonate (0.091 g) in acetonitrile (0.4 mL) was added benzyl(2-bromoethyl)ether (0.035 mL), and the mixture was stirred at 80° C. for 30 minutes. After cooling to room temperature, the reaction mixture was further stirred overnight. To the reaction mixture were added methanol (0.4 mL) and 2 mol/L aqueous sodium hydroxide solution (0.55 mL), and the mixture was stirred at room temperature for 1 hour. Water was added to the reaction mixture, and the mixture was purified by CBA solid phase extraction (washing solvent: distilled water, eluent: methanol), and successively by column chromatography on silica gel (eluent: dichloromethane/methanol=10/1-5/1) to give to give 1-(2-benzyloxyethyl)-4-[(4-ethylphenyl)methyl]-3-(β-D-glucopyranosyloxy)-5-methyl-1H-pyrazole (0.012 g).

$^1$H-NMR (CD$_3$OD) δ ppm: 1.17 (3H, t, J=7.6 Hz), 2.08 (3H, s), 2.56 (2H, q, J=7.6 Hz), 3.25–3.45 (4H, m), 3.60–3.90 (6H, m), 4.05–4.20 (2H, m), 4.30–4.45 (2H, m), 5.00–5.10 (1H, m), 7.00–7.30 (9H, m)

REFERENCE EXAMPLE 19

5-Methyl-4-[(4-methylthiophenyl)methyl]-1,2-dihydro-3H-pyrazol-3-one

The title compound was prepared in a similar manner to that described in Reference Example 16 using 4-methylthiobenzyl alcohol instead of 4-ethylbenzyl alcohol.
$^1$H-NMR (DMSO-$d_6$) δ ppm: 1.99 (3H, s), 2.42 (3H, s), 3.50 (2H, s), 7.05–7.20 (4H, m)

REFERENCE EXAMPLE 20

5-Methyl-4-[(methylthiophenyl)methyl]-3-(2,3,4,6-tetra-O-acetyl-β-D-glucopyranosyloxy)-1H-pyrazole The title compound was prepared in a similar manner to that described in Reference Example 17 using 5-methyl-4-[(4-methylthiophenyl)methyl]-1,2-dihdro-3H-pyrazole-3-one instead of 4-[(4-ethylphenyl)methyl]-5-methyl-1,2-dihdro-3H-pyrazol-3-one.
$^1$H-NMR (CDCl$_3$) δ ppm: 1.88 (3H, s), 2.01 (3H, s), 2.03 (3H, s), 2.07 (3H, s), 2.12 (3H, s), 2.44 (3H, s), 3.50–3.65 (2H, m), 3.80–3.90 (1H, m), 4.13 (1H, dd, J=2.4, 12.4 Hz), 4.31 (1H, dd, J=4.1, 12.4 Hz), 5.15–5.30 (3H, m), 5.55–5.65 (1H, m), 7.00–7.10 (2H, m), 7.10–7.20 (2H, m), 8.65–8.85 (1H, brs)

REFERENCE EXAMPLE 21

3-(β-D-Glucopyranosyloxy)-5-methyl-4-[(4-methylthiophenyl)methyl]-1H-pyrazole

To a solution of 5-methyl-4-[(methylthiophenyl)methyl]-3-(2,3,4,6-tetra-O-acetyl-β-D-glucopyranosyloxy)-1H-pyrazole (0.42 g) in ethanol (5 mL) was added sodium methoxide (28% methanol solution, 0.042 mL), and the mixture was stirred at room temperature for 1 hour. The reaction mixture was concentrated under reduced pressure, and the residue was purified by column chromatography on silica gel (eluent: dichloromethane/methanol=5/1) to give 3-(β-D-glucopyranosyloxy)-5-methyl-4-[(4-methylthiophenyl)methyl]-1H-pyrazole (0.23 g).
$^1$H-NMR (CD$_3$OD) δ ppm: 2.06 (3H, s), 2.42 (3H, s), 3.20–3.45 (4H, m), 3.55–3.75(3H, m), 3.80–3.90 (1H, m), 5.00–5.10 (1H, m), 7.05–7.20 (4H, m)

REFERENCE EXAMPLE 22

4-[(4-Isopropoxyphenyl)methyl]-5-methyl-1,2-dihdro-3H-pyrazol-3-one

To a solution of 4-isopropoxybenzyl alcohol (0.34 g) in tetrahydrofuran (6 mL) were added triethylamine (0.28 mL) and methanesulfonyl chloride (0.16 mL), and the mixture was stirred at room temperature for 30 minutes. Insoluble materials were removed by filtration. A solution of the obtained 4-isopropoxybenzyl methanesulfonate in tetrahydrofuran was added to a suspension of sodium hydride (60%, 81 mg) and methyl acetoacetate (0.20 mL) in 1,2-dimethoxyethane (10 mL), and the mixture was stirred at 80° C. overnight. The reaction mixture was poured into a saturated aqueous sodium hydrogen carbonate solution, and the mixture was extracted with diethyl ether. The organic layer was washed with brine and dried over anhydrous magnesium sulfate. The solvent was removed under reduced pressure, and the residue was dissolved in toluene (5 mL). To the mixture was added anhydrous hydrazine (0.19 mL), and the mixture was stirred at 80° C. overnight. The solvent was removed under reduced pressure, and the residue was purified by column chromatography on silica gel (eluent: dichloromethane/methanol=10/1) to give 4-[(4-isopropoxyphenyl)methyl]-5-methyl-1,2-dihydro-3H-pyrazol-3-one (95 mg).
$^1$H-NMR (DMSO-$d_6$) δ ppm: 1.22 (6H, d, J=6.0 Hz), 1.99 (3H, s), 3.45 (2H, s), 4.40–4.60 (1H, m), 6.65–6.80 (2H, m), 6.95–7.10 (2H, m)

REFERENCE EXAMPLE 23

4-[(4-Isopropoxyphenyl)methyl]-5-methyl-3-(2,3,4,6-tetra-O-acetyl-β-D-glucopyranosyloxy)-1H-pyrazole To a suspension of 4-[(4-isopropoxyphenyl)methyl]-5-methyl-1,2-dihydro-3H-pyrazol-3-one (46 mg), acetobromo-α-D-glucose (99 mg) and 4A molecular sieves in tetrahydrofuran (3 mL) was added silver carbonate (66 mg), and the mixture was stirred at 65° C. overnight under light shielding. The reaction mixture was purified by column chromatography on aminopropyl silica gel (eluent: tetrahydrofuran), and successively by preparative thin layer chromatography on silica gel (developing solvent: ethyl acetate/hexane=2/1) to give 4-[(4-isopropoxyphenyl)methyl]-5-methyl-3-(2,3,4,6-tetra-O-acetyl-β-D-glucopyranosyloxy)-1H-pyrazole (42 mg).
$^1$H-NMR (CDCl$_3$) δ ppm: 1.25–1.35 (6H, m), 1.88 (3H, s), 2.01 (3H, s), 2.03 (3H, s), 2.05 (3H, s), 2.10 (3H, s), 3.45–3.65 (2H, m), 3.80–3.90 (1H, m), 4.13 (1H, dd, J=2.3, 12.4 Hz), 4.31 (1H, dd, J=4.0, 12.4 Hz), 4.40–4.55 (1H, m), 5.15–5.35 (3H, m), 5.50–5.60 (1H, m), 6.70–6.80 (2H, m), 6.95–7.05 (2H, m)

REFERENCE EXAMPLE 24

3-(β-D-Glucopyranosyloxy)-4-[(4-isopropoxyphenyl)methyl]-5-methyl-1H-pyrazole

To a solution of 4-[(4-isopropoxyphenyl)methyl]-5-methyl-3-(2,3,4,6-tetra-O-acetyl-β-D-glucopyranosyloxy)-1H-pyrazole (61 mg) in ethanol (3 mL) was added 1 mol/L aqueous sodium hydroxide solution (0.53 mL), and the mixture was stirred at room temperature for 2 hours. The solvent was removed under reduced pressure, and the residue was purified by solid phase extraction on ODS (washing solvent: distilled water, eluent: methanol) to give 3-(β-D-glucopyranosyloxy)-4-[(4-isopropoxyphenyl)methyl]-5-methyl-1H-pyrazole (39 mg).
$^1$H-NMR (CD$_3$OD) δ ppm: 1.26 (6H, d, J=5.9 Hz), 2.05 (3H, s), 3.25–3.45 (4H, m), 3.55–3.75 (3H, m), 3.75–3.90 (1H, m), 4.45–4.60 (1H, m), 5.00–5.10 (1H, m), 6.70–6.80 (2H, m), 7.00–7.15 (2H, m)

EXAMPLE 35

4-[(4-Ethylphenyl)methyl]-3-(β-D-glucopyranosyloxy)-1-(2-hydroxyethyl)-5-methyl-1H-pyrazol To a solution of 1-(2-benzyloxyethyl)-4-[(4-ethylphenyl)methyl]-3-(β-D-glucopyranosyloxy)-5-methyl-1H-pyrazole (0.012 g) in ethanol (2 mL) was added a catalytic amount of 10% palladium-carbon powder, and the mixture was stirred at room temperature under a hydrogen atmosphere for 30 minutes. Insoluble materials were removed by filtration, and the solvent was removed under reduced pressure to give 4-[(4-ethylphenyl)methyl]-3-(β-D-glucopyranosyloxy)-1-(2-hydroxyethyl-5-methyl-1H-pyrazole (0.011 g).

$^1$H-NMR (CD$_3$OD) δ ppm: 1.18 (3H, t, J=7.6 Hz), 2.11 (3H, s), 2.56 (2H, q, J=6Hz), 3.25–3.50 (4H, m), 3.55–3.95 (6H, m), 3.95–4.05 (2H, m), 5.05–5.15 (1H, m), 7.00–7.15 (4H, m)

EXAMPLE 36

3-(β-D-Glucopyranosyloxy)-1-(3-hydroxypropyl)-5-methyl-4-[(4-methylthiophenyl)methyl]-1H-pyrazole To a suspension of 3-(β-D-glucopyranosyloxy)-5-methyl-4-[(4-methylthiophenyl)methyl]-1H-pyrazole (0.020 g) and cesium carbonate (0.11 g) in N,N-dimethylformamide (0.5 mL) was added 3-bromopropanol (0.022 mL), and the mixture was stirred at 40° C. overnight. To the reaction mixture was added water, and the mixture was purified by solid phase extraction on ODS (washing solvent: distilled water, eluent: methanol), and successively by column chromatography on silica gel (eluent: dichloromethane/methanol=5/1) to give 3-(β-D-glucopyranosyloxy)-1-(3-hydroxypropyl)-5-methyl-4-[(4methylthiophenyl)methyl]-1H-pyrazole (0.011 g).

$^1$H-NMR (CD$_3$OD) δ ppm: 1.85–1.95 (2H, m), 2.10 (3H, s), 2.42 (3H, s), 3.25–3.45 (4H, m), 3.45–3.55 (2H, m), 3.60–3.75 (3H, m), 3.82 (1H, dd, J=1.8, 12.2 Hz), 3.95–4.10 (2H, m), 5.00–5.15 (1H, m), 7.05–7.20 (4H, m)

EXAMPLE 37

1-Allyl-4-[(4-ethylphenyl)methyl]-3-(β-D-glucopyranosyloxy)-5-methyl-1H-pyrazole To a suspension of 4-[(4-ethylphenyl)methyl]-5-methyl-3-(2,3,4,6-tetra-O-acetyl-β-D-glucopyranosyloxy)-1H-pyrazole (0.030 g) and cesium carbonate (0.036 g) in acetonitrile (0.4 mL) was added allyl iodide (0.010 mL), and the mixture was stirred at room temperature for 1 hour. To the reaction mixture were added methanol (0.4 mL) and 1 mol/L aqueous sodium hydroxide solution (0.5 mL), and the mixture was stirred at room temperature for 1 hour. Water was added to the reaction mixture, and the mixture was purified by solid phase extraction on ODS (washing solvent: distilled water, eluent: methanol), and successively by column chromatography on silica gel (eluent: dichloromethane/methanol=10/1) to give 1-allyl-4-[(4-ethylphenyl)methyl]-3-(β-D-glucopyranosyloxy)-5-methyl-1H-pyrazole (0.018 g).

$^1$H-NMR (CD$_3$OD) δ ppm: 1.18 (3H, t, J=7.5 Hz), 2.04 (3H, s), 2.57 (2H, q, J=7.5 Hz), 3.25–3.45 (4H, m), 3.55–3.95 (4H, m), 4.50–4.65 (2H, m), 4.80–4.95 (1H, m), 5.00–5.20 (2H, m), 5.85–6.00 (1H, m), 7.00–7.15 (4H, m)

EXAMPLE 38

1-(Cyclopropylmethyl)-3-(β-D-glucopyranosyloxy)-5-methyl-4-[(4-methylthiophenyl)methyl]-1H-pyrazole To a solution of 3-(β-D-glucopyranosyloxy)-5-methyl-4-[(4-methylthiophenyl)methyl]-1H-pyrazole (0.081 g) in N,N-dimethylformamide (1 mL) were added cesium carbonate (0.40 g), bromomethylcyclopropane (0.099 mL) and a catalytic amount of sodium iodide, and the mixture was stirred at room temperature for 7 days. Water was added to the reaction mixture, and the mixture was extracted with ethyl acetate. The organic layer was washed with water, and dried over anhydrous magnesium sulfate, and the solvent was removed under reduced pressure. The residue was purified by column chromatography on silica gel (eluent: dichloromethane/methanol=10/1-8/1) to give 1-(cyclopropylmethyl)-3-(β-D-glucopyranosyloxy)-5-methyl-4-[(4methylthiophenyl)methyl]-1H-pyrazole (0.041 g).

$^1$H-NMR (CD$_3$OD) δ ppm: 0.25–0.40 (2H, m), 0.40–0.60 (2H, m), 1.05–1.25 (1H, m), 2.10 (3H, s), 2.42 (3H, s), 3.25–3.45 (4H, m), 3.55–3.90 (6H, m), 5.00–5.10 (1H, m), 7.00–7.25 (4H, m)

EXAMPLE 39

4-[(4-Ethylphenyl)methyl]-3-(β-D-glucopyranosyloxy)-1-(3-hydroxypropyl)-5-methyl-1H-pyrazole To a suspension of 4-[(4-ethylphenyl)methyl]-5-methyl-3-(2,3,4,6-tetra-O-acetyl-β-D-glucopyranosyloxy)-1H-pyrazole (0.030 g) and cesium carbonate (0.091 g) in acetonitrile (0.4 mL) was added benzyl(3-bromopropyl) ether (0.039 mL), and the mixture was stirred at 80° C. for 30 minutes. To the reaction mixture were added methanol (0.4 mL) and 2 mol/L aqueous sodium hydroxide solution (0.55 mL), and the mixture was stirred at room temperature overnight. Water was added to the reaction mixture, and the mixture was purified by solid phase extraction on ODS (washing solvent: distilled water, eluent: methanol). To the resulting eluent was added a catalytic amount of 10% palladium-carbon powder, and the mixture was stirred at room temperature under a hydrogen atmosphere for 3 days. Insoluble materials were removed by filtration, and the solvent of the filtrate was removed under reduced pressure. The residue was purified by liquid chromatography on ODS (eluent: methanol/water=40/60) to give 4-[(4-ethylphenyl)methyl]-3-(β-D-glucopyranosyloxy)-1-(3-hydroxypropyl)-5-methyl-1H-pyrazole (0.0080 g).

$^1$H-NMR (CD$_3$OD) δ ppm: 1.18 (3H, t, J=7.5 Hz), 1.85–2.00 (2H, m), 2.10 (3H, s), 2.57 (2H, q, J=7.5 Hz), 3.25–3.45 (4H, m), 3.45–3.55 (2H, m), 3.55–3.90 (4H, m), 3.95–4.10 (2H, m), 5.00–5.10 (1H, m), 7.00–7.15 (4H, m)

EXAMPLE 40

1-(Cyclopropylmethyl)-3-(β-D-glucopyranosyloxy)-4-[(4-isopropoxyphenyl)methyl]-5-methyl-1H-pyrazole To a suspension of 3-(β-D-glucopyranosyloxy)-4-[(4-isopropoxyphenyl)methyl]-5-methyl-1H-pyrazole (0.050 g) cesium carbonate (0.20 g) and a catalytic amount of sodium iodide in N,N-dimethylformamide (1 mL) was added bromomethylcyclopropane (0.050 g) at 50° C., and the mixture was stirred for 3 days. Water was added to the reaction mixture, and the mixture was purified by solid phase extraction on ODS (washing solvent: distilled water, eluent: methanol), and successively by column chromatography on silica gel (eluent: dichloromethane/methanol=8/1) to give 1-(cyclopropylmethyl)-3-(β-D-glucopyranosyloxy)-4-[(4-isopropoxyphenyl)methyl]-5-methyl-1H-pyrazole (0.034 g).

$^1$H-NMR (CD$_3$OD) δ ppm: 0.25–0.35 (2H, m), 0.45–0.55 (2H, m), 1.10–1.25 (1H, m), 1.26 (6H, d, J=6.1 Hz), 2.09 (3H, s), 3.25–3.45 (4H, m), 3.55–3.75 (3H, m), 3.75–3.90 (3H, m), 4.45–4.55 (1H, m), 5.00–5.10 (1H, m), 6.70–6.85 (2H, m), 7.00–7.15 (2H, m)

EXAMPLE 41

1-Cyclopentyl-3-(β-D-glucopyranosyloxy)-4-[(4-isopropoxyphenyl)methyl]-5-methyl-1H-pyrazole To a suspension of 3-(β-D-glucopyranosyloxy)-4-[(4-isopropoxyphenyl)methyl]-5-methyl-1H-pyrazole (0.050 g) and cesium carbonate (0.20 g) in N,N-dimethylformamide (1 mL) was added cyclopentyl bromide (0.055 g) at 80° C., and the mixture was stirred for 30 minutes. After cooling to room temperature, water was added to the reaction mixture, and the mixture was purified by solid phase extraction on ODS (washing solvent: distilled water, eluent: methanol), and successively by column chromatography on silica gel (eluent: dichloromethane/methanol=8/1) to give 1-cyclopentyl-3-(β-D-glucopyranosyloxy)-4-[(4-isopropoxyphenyl)methyl]-5-methyl-1H-pyrazole (0.034 g).

$^1$H-NMR (CD$_3$OD) δ ppm: 1.26 (6H, d, J=6.1 Hz), 1.55–1.75 (2H, m), 1.80–2.05 (6H, m), 2.03 (3H, s), 3.15–3.30 (1H, m), 3.30–3.45 (3H, m), 3.60–3.75 (3H, m), 3.77 (1H, dd, J=2.6, 12.0 Hz), 4.40–4.65 (2H, m), 5.00–5.10 (1H, m), 6.70–6.85 (2H, m), 7.00–7.15 (2H, m)

EXAMPLE 42

1-(Cyclopropylmethyl)-4-[(4-isopropoxyphenyl)methyl]-5-methyl-3-(6-O-propionyl-β-D-glucopyranosyloxy)-1H-pyrazole To a solution of 1-(cyclopropylmethyl)-3-(β-D-glucopyranosyloxy)-4-[(4-isopropoxyphenyl)methyl]-5-methyl-1H-pyrazole (0.40 g) in 2,4,6-trimethylpyridine (1.5 mL) was added propionyl chloride (0.0088 g) at 0° C., and the mixture was stirred for 3 hours. Citric acid monohydrate (3.3 g) and water were added to the reaction mixture, and the mixture was purified by solid phase extraction on ODS (washing solvent: distilled water, eluent: methanol), and successively by column chromatography on silica gel (eluent: dichloromethane/methanol=10/1) to give 1-(cyclopropylmethyl)-4-[(4-isopropoxyphenyl)methyl]-5-methyl-3-(6-O-propionyl-β-D-glucopyranosyloxy)-1H-pyrazole (0.20 g).

$^1$H-NMR (CD$_3$OD) δ ppm: 0.25–0.35 (2H, m), 0.45–0.55 (2H, m), 1.05 (3H, t, J=7.6 Hz), 1.15–1.25 (1H, m), 1.26 (6H, d, J=6.3 Hz), 2.07 (3H, s), 2.29 (2H, q, J=7.6 Hz), 3.30–3.55 (4H, m), 3.55–3.70 (2H, m), 3.82 (2H, d, J=6.7 Hz), 4.22 (1H, dd, J=5.4, 12.0 Hz), 4.32 (1H, dd, J=2.3, 12.0 Hz), 4.45–4.55 (1H, m), 5.05–5.15 (1H, m), 6.70–6.80 (2H, m), 7.00–7.15 (2H, m)

EXAMPLE 43

1-(Cyclopropylmethyl)-3-(6-O-ethoxycarbonyl-β-D-glucopyranosyloxy)-4-[(4-isopropoxyphenyl)methyl]-5-methyl-1H-pyrazole To a solution of 1-(cyclopropylmethyl)-3-(β-D-glucopyranosyloxy)-4-[(4-isopropoxyphenyl)methyl]-5-methyl-1H-pyrazole (0.050 g) in 2,4,6-trimethylpyridine (1 mL) was added ethyl chloroformate (0.035 g), and the mixture was stirred at room temperature overnight. Citric acid monohydrate (3.3 g) and water were added to the reaction mixture, and the mixture was purified by solid phase extraction on ODS (washing solvent: distilled water, eluent: methanol), and successively by column chromatography on silica gel (eluent: dichloromethane/methanol=10/1) to give 1-(cyclopropylmethyl)-3-(6-O-ethoxycarbonyl-β-D-glucopyranosyloxy)-4-[(4-isopropoxyphenyl)methyl]-5-methyl-1H-pyrazole (0.043 g).

$^1$H-NMR (CD$_3$OD) δ ppm: 0.25–0.35 (2H, m), 0.45–0.55 (2H, m), 1.05–1.25 (1H, m) 1.25 (3H, t, J=7.1 Hz), 1.26 (6H, d, J=6.1 Hz), 2.08 (3H, s), 3.30–3.50 (4H, m), 3.62 (1H, d, J=16.2 Hz), 3.67 (1H, d, J=16.2 Hz), 3.82 (2H, d, J=6.6 Hz), 4.13 (2H, q, J=7.1 Hz), 4.23 (1H, dd, J=5.2, 11.7 Hz), 4.37 (1H, dd, J=2.1, 11.7 Hz), 4.45–4.55 (1H, m), 5.05–5.15 (1H, m), 6.70–6.80 (2H, m), 7.00–7.15 (2H, m)

TEST EXAMPLE 1

Assay for Inhibitory Effect on Human SGLT2 Activity

1) Construction of the Plasmid Vector Expressing Human SGLT2

Preparation of the cDNA library for PCR amplification was performed by reverse transcription of a total RNA deprived from human kidney (Ori gene) with oligo dT as the primer, using SUPERSCRIPT Preamplification System (Gibco-BRL: LIFE TECHNOLOGIES). The DNA fragment coding for human SGLT2 was amplified by the PCR reaction, in which the human kidney cDNA library described above was used as the template and the following oligo nucleotides 0702F and 0712R, presented as Sequence Numbers 1 and 2 respectively, were used as the primers. The amplified DNA fragment was ligated into pCR-Blunt (Invitrogen), a vector for cloning, according to standard method of the kit. The *Escherichia coli* HB101 was transformed according to usual method and then selection of the transformants was performed on the LB agar medium containing 50 μg/mL of kanamycin. After plasmid DNA was extracted and purified from the one of the transformants, amplifying of the DNA fragment coding for human SGLT2 was performed by the PCR reaction, in which the following oligo nucleotides 0714F and 0715R, presented as Sequence Numbers 3 and 4 respectively, were used as the primers. The amplified DNA fragment was digested with restriction enzymes, Xho I and Hind III, and then purified with Wizard Purification System (Promega). This purified DNA fragment was inserted at the corresponding restriction sites of pcDNA3.1 (−) Myc/His-B (Invitrogen), a vector for expressing of fusion protein. The *Escherichia coli* HB101 was transformed according to usual method and then selection of the transformant was performed on the LB agar medium containing 100 μg/mL of ampicillin. After plasmid DNA was extracted and purified from this transformant, the base sequence of the DNA fragment inserted at the multi-cloning sites of the vector pcDNA3.1 (−) Myc/His-B was analyzed. This clone had a single base substitution (ATC which codes for the isoleucine-433 was substituted by GTC) compared with the human SGLT2 reported by Wells et al (Am. J. Physiol., Vol. 263, pp. 459–465 (1992)). Sequentially, a clone in which valine is substituted for isoleucine-433 was obtained. This plasmid vector expressing human SGLT2 in which the peptide presented as Sequence Number 5 is fused to the carboxyl terminal alanine residue was designated KL29.

Sequence Number 1    ATGGAGGAGCACACAGAGGC

Sequence Number 2    GGCATAGAAGCCCCAGAGGA

```
                  -continued
Sequence Number 3    AACCTCGAGATGGAGGAGCACACAGAGGC Sequence Number 4    AACAAGCTTGGCATAGAAGCCCCAGAGGA Sequence Number 5    KLGPEQKLISEEDLNSAVDHHHHHH
```

2) Preparation of the Cells Expressing Transiently Human SGLT2

KL29, the plasmid coding human SGLT2, was transfected into COS-7 cells (RIKEN CELL BANK RCB0539) by electroporation. Electroporation was performed with GENE PULSER II (Bio-Rad Laboratories) under the condition: 0.290 kV, 975 μF, $2\times10^6$ cells of COS-7 cell and 20 μg of KL29 in 500 μL of OPTI-MEM I medium (Gibco-BRL: LIFE TECHNOLOGIES) in the 0.4 cm type cuvette. After the gene transfer, the cells were harvested by centrifugation and resuspended with OPTI-MEM I medium (1 mL/cuvette). To each well in 96-wells plate, 125 μL of this cell suspension was added. After overnight culture at 37° C. under 5% $CO_2$, 125 μL of DMEM medium which is containing 10% of fetal bovine serum (Sanko Jyunyaku), 100 units/mL sodium penicillin G (Gibco-BRL: LIFE TECHNOLOGIES), and 100 μg/mL streptomycin sulfate (Gibco-BRL: LIFE TECHNOLOGIES) was added to each well. These cells were cultured until the next day and then they were used for the measurement of the inhibitory activity against the uptake of methyl-α-D-glucopyranoside.

3) Measurement of the Inhibitory Activity Against the Uptake of Methyl-α-D-glucopyranoside After a test compound was dissolved in dimethyl sulfoxide and diluted with the uptake buffer (a pH 7.4 buffer containing 140 mM sodium chloride, 2 mM potassium chloride, 1 mM calcium chloride, 1 mM magnesium chloride, 5 mM methyl-α-D-glucopyranoside, 10 mM 2-[4-(2-hydroxyethyl)-1-piperazinyl]ethane sulfonic acid and 5 mM tris(hydroxymethyl)aminomethane), each diluent was used as test sample for measurement of the inhibitory activity. After removal of the medium of the COS-7 cells expressing transiently human SGLT2, to each well 200 μL of the pretreatment buffer (a pH 7.4 buffer containing 140 mM choline chloride, 2 mM potassium chloride, 1 mM calcium chloride, 1 mM magnesium chloride, 10 mM 2-[4-(2-hydroxyethyl)-1-piperazinyl]ethane sulfonic acid and 5 mM tris(hydroxymethyl)aminomethane) was added, and the cells were incubated at 37° C. for 10 minutes. After the pretreatment buffer was removed, 200 μL of the same buffer was added again, and the cells were incubated at 37° C. for 10 minutes. The buffer for measurement was prepared by adding and mixing 7 μL of methyl-α-D-(U-14C)glucopyranoside (Amersham Pharmacia Biotech) to 525 μL of the prepared test sample. For the control, the buffer for measurement without any test compound was prepared. For estimate of the basal uptake in the absence of a test compound and sodium, the buffer for measurement of the basal uptake, which contains 140 mM choline chloride in place of sodium chloride, was prepared similarly. After the pretreatment buffer was removed, 75 μL of the each buffer for measurement was added to each well, and the cells were incubated at 37° C. for 2 hours. After the buffer for measurement was removed, 200 μL of the washing buffer (a pH 7.4 buffer containing 140 mM choline chloride, 2 mM potassium chloride, 1 mM calcium chloride, 1 mM magnesium chloride, 10 mM methyl-α-D-glucopyranoside, 10 mM 2-[4-(2-hydroxyethyl)-1-piperazinyl]ethane sulfonic acid and 5 mM tris(hydroxymethyl)aminomethane) was added to each well and immediately removed. After two additional washing, the cells were solubilized by addition of 75 μL of 0.2 mol/L aqueous sodium hydroxide solution to each well. After the cell lysates were transferred to the PicoPlate (Packard) and 150 μL of MicroScint-40 (Packard) was added to each well, the radioactivity was measured with microplate scintillation counter TopCount (Packard). The difference in uptake was obtained as 100% value by subtracting the radioactivity in the basal uptake from that in control and then the concentrations at which 50% of uptake were inhibited ($IC_{50}$) were calculated from the concentration-inhibition curve by least square method. The results are shown in the following Table 1.

TABLE 1

| Test compound | $IC_{50}$ value (nM) |
|---|---|
| Example 20 | 15 |
| Example 21 | 18 |
| Example 22 | 41 |
| Example 23 | 46 |
| Example 24 | 57 |
| Example 25 | 65 |
| Example 26 | 150 |
| Example 27 | 210 |
| Example 32 | 26 |
| Example 38 | 45 |
| Example 39 | 47 |
| WAY-123783 | >100000 |

INDUSTRIAL APPLICABILITY

The glucopyranosyloxyboyrazole derivatives represented by the above general formula (I) of the present invention, pharmaceutically acceptable salts thereof and prodrugs thereof show an excellent hypoglycemic effect by excreting excess glucose into the urine through preventing the reabsorption of glucose at the kidney because they exhibit an excellent inhibitory activity in human SGLT2. The present invention can provide drugs for the prevention or treatment of a disease associated with hyperglycemia such as diabetes, diabetic complications, obesity or the like. In addition, since compounds represented by the above general formula (III) or (IV) or salts thereof are important as intermediates in the production of the compounds represented by the above general formula (I), pharmaceutically acceptable salts thereof and prodrugs thereof, the compounds represented by the above general formula (I), pharmaceutically acceptable salts thereof and prodrugs thereof of the present invention can be readily prepared via such compounds.

[Sequence Listing Free Text]

Sequence Number 1: Synthetic DNA primer

Sequence Number 2: Synthetic DNA primer

Sequence Number 3: Synthetic DNA primer

Sequence Number 4: Synthetic DNA primer

Sequence Number 5: Peptide fused to the carboxyl terminal alanine residue of human SGLT2

The invention claimed is:

1. A glucopyranosyloxypyrazole derivative represented by the general formula:

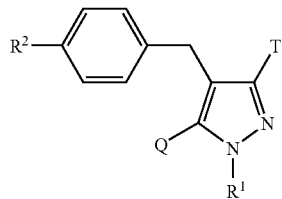

wherein one of Q and T represents a group represented by the general formula:

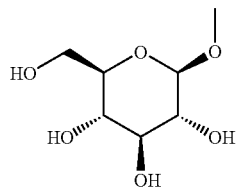

while the other represents a lower alkyl group or a halo (lower alkyl) group; $R^1$ represents a hydrogen atom, a lower alkyl group, a lower alkenyl group, a cyclic lower alkyl group, a cyclic lower alkyl-substituted (lower alkyl) group or a group represented by the general formula: HO-A- wherein A represents a lower alkylene group; $R^2$ represents a lower alkenyl group, a cyclic lower alkyl group, a cyclic lower alkoxy group, a cyclic lower alkylidenemethyl group, a phenyl group which may have 1–3 different or same groups selected from a halogen atom or a hydroxy group, a 5 or 6-membered aromatic heterocyclic group which contains 1–4 different or same atoms selected from an oxygen atom, a sulfur atom or a nitrogen atom in the ring, or a group represented by the general formula: HO-$A^2$- wherein 2 represents a lower alkylene group; or a pharmaceutically acceptable salt thereof.

2. A pharmaceutical composition comprising as an active ingredient a glucopyranosyloxypyrazole derivative as claimed in claim 1 or a pharmaceutically acceptable salt thereof in combination with a pharmaceutically acceptable additive.

3. A glucopyranosyloxypyrazole derivative represented by the general formula:

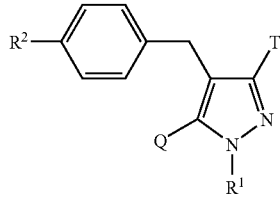

wherein one of Q and T represents a group represented by the general formula:

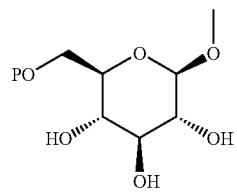

while the other represents a lower alkyl group or a halo (lower alkyl) group; $R^1$ represents a lower alkenyl group, a cyclic lower alkyl group, a cyclic lower alkyl-substituted (lower alkyl) group or a group represented by the general formula: HO-$A^1$- wherein $A^1$ represents a lower alkylene group; $R^2$ represents a hydrogen atom, a lower alkyl group, a lower alkoxy group, a lower alkylthio group, a halo(lower alkyl) group or a halogen atom; or a pharmaceutically acceptable salt thereof.

4. A pharmaceutical composition comprising as an active ingredient a glucopyranosyloxypyrazole derivative as claimed in claim 3, or a pharmaceutically acceptable salt thereof in combination with a pharmaceutically acceptable additive.

* * * * *

SEQUENCE LISTING

<160> NUMBER OF SEQ ID NOS: 5

<210> SEQ ID NO 1
<211> LENGTH: 20
<212> TYPE: DNA
<213> ORGANISM: Artificial Sequence
<220> FEATURE:
<223> OTHER INFORMATION: Synthetic DNA primer

<400> SEQUENCE: 1
atggaggagc acacagaggc                                                    20

<210> SEQ ID NO 2
<211> LENGTH: 20
<212> TYPE: DNA
<213> ORGANISM: Artificial Sequence
<220> FEATURE:
<223> OTHER INFORMATION: Synthetic DNA primer

<400> SEQUENCE: 2
ggcatagaag ccccagagga                                                    20

<210> SEQ ID NO 3
<211> LENGTH: 29
<212> TYPE: DNA
<213> ORGANISM: Artificial Sequence
<220> FEATURE:
<223> OTHER INFORMATION: Synthetic DNA primer

<400> SEQUENCE: 3
aacctcgaga tggaggagca cacagaggc                                          29

<210> SEQ ID NO 4
<211> LENGTH: 29
<212> TYPE: DNA
<213> ORGANISM: Artificial Sequence
<220> FEATURE:
<223> OTHER INFORMATION: Synthetic DNA primer

<400> SEQUENCE: 4
aacaagcttg gcatagaagc cccagagga                                          29

<210> SEQ ID NO 5
<211> LENGTH: 25
<212> TYPE: PRT
<213> ORGANISM: Artificial Sequence
<220> FEATURE:
<223> OTHER INFORMATION: Peptide fused to the carboxyl terminal alanine
                        residue of human SGLT2

<400> SEQUENCE: 5

Lys Leu Gly Pro Glu Gln Lys Leu Ile Ser Glu Glu Asp Leu Asn Ser
1               5                   10                  15

Ala Val Asp His His His His His His
            20                  25